US007524491B2

(12) United States Patent
Goldman et al.

(10) Patent No.: US 7,524,491 B2
(45) Date of Patent: Apr. 28, 2009

(54) NON HUMAN ANIMALS WITH HUMAN-GLIAL CHIMERIC BRAINS

(75) Inventors: Steven A. Goldman, Webster, NY (US); Martha Windrem, West Henrietta, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/015,372

(22) Filed: Jan. 16, 2008

(65) Prior Publication Data

US 2008/0184378 A1 Jul. 31, 2008

Related U.S. Application Data

(60) Provisional application No. 60/885,094, filed on Jan. 16, 2007.

(51) Int. Cl.
*G01N 33/00* (2006.01)
*A01K 67/00* (2006.01)
*A01K 67/033* (2006.01)
*C12N 15/00* (2006.01)

(52) U.S. Cl. ............................. 424/93.1; 800/8; 800/3; 800/21

(58) Field of Classification Search .................... 800/8, 800/3; 424/93.1
See application file for complete search history.

(56) References Cited

U.S. PATENT DOCUMENTS 6,497,872 B1   12/2002  Weiss et al.
2004/0029269 A1*  2/2004  Goldman et al. ............ 435/368

OTHER PUBLICATIONS

Windrem (Nature Med., 2004, vol. 10, No. 1, p. 93-97).*
Nunes (Nature Med. Apr. 2003, vol. 9, No. 4, p. 439-447).*
Nunes et al., "Identification and Isolation of Multipotential Neural Progenitor Cells for the Subcortical White Matter of the Adult Human Brain," Natural Medicine 9(4):439-47 (2003).
Windrem et al., "Fetal and Adult Human Oligodendrocyte Progenitor Cell Isolates Myelinate the Congenitally Dysmyelinated Brain," Nature Medicine 10(1):93-7 (2004).

* cited by examiner

*Primary Examiner*—Michael C. Wilson
(74) *Attorney, Agent, or Firm*—Nixon Peabody LLP

(57) ABSTRACT

The present invention is directed to a non-human mammal with at least 30% of all of its glial cells in its corpus callosum being human glial cells and/or at least 5% of all of its glial cells in the white matter of its brain and/or brain stem being human glial cells. Methods of producing and using the non-human mammal are also disclosed.

50 Claims, 7 Drawing Sheets

NON HUMAN ANIMALS WITH HUMAN-GLIAL CHIMERIC BRAINS

This application claims the benefit of U.S. Provisional Patent Application Ser. No. 60/885,094, filed Jan. 16, 2007.

FIELD OF THE INVENTION

The present application relates to non-human animals with human glial chimeric brains.

BACKGROUND OF THE INVENTION

Glial progenitor cells and the neural stem cells from which they derive may be isolated and transplanted into myelin-deficient hosts, as a means of introducing new oligodendrocytes able to myelinate host axons (Yandava et al., "Global Cell Replacement is Feasible Via Neural Stem Cell Transplantation: Evidence From the Dysmyelinated Shiverer Mouse Brain," *Proc Natl Acad Sci USA* 96:7029-34 (1999); Learish et al., "Intraventricular Transplantation of Oligodendrocyte Progenitors Into a Fetal Myelin Mutant Results in Widespread Formation of Myelin," *Ann Neurol* 46:716-22 (1999); Archer et al., "Myelination of the Canine Central Nervous System by Glial Cell Transplantation: A Model for Repair of Human Myelin Disease," *Nature Medicine* 3:54-59 (1997); Mitome et al., "Towards the Reconstruction of Central Nervous System White Matter Using Neural Precursor Cells," *Brain* 124:2147-61 (2001); Eftekharpour et al., "Myelination of Congenitally Dysmyelinated Spinal Cord Axons by Adult Neural Precursor Cells Results in Formation of Nodes of Ranvier and Improved Axonal Conduction," *J Neuroscience* 27:3416-3428 (2007)). Applicants have previously noted that enriched preparations of human glial progenitor cells, when engrafted into the neonatal shiverer mouse, a mutant that lacks full-length myelin basic protein (Roach et al., "Chromosomal Mapping of Mouse Myelin Basic Protein Gene and Structure and Transcription of the Partially Deleted Gene in Shiverer Mutant Mice," *Cell* 42:149-55 (1985)), generate substantial myelin in these otherwise unmyelinated recipients (Windrem et al., "Fetal and Adult Human Oligodendrocyte Progenitor Cell Isolates Myelinate the Congenitally Dysmyelinated Brain," *Nature Medicine* 10:93-97 (2004)). However, the potential utility of this approach to the development of clinical remyelination strategies has been unclear, since previous studies have failed to note significant brainstem, cerebellar or spinal engraftment from intracerebral grafts, and no effect on disease phenotype or survival has yet been reported in hypomyelinated mice as a consequence of progenitor cell transplantation (reviewed in Keyoung et al., "Glial Progenitor-Based Repair of Demyelinating Neurological Diseases," *Neurosurg. Clin. NA* 18:93-104 (2007) and Goldman, S. A., "Stem and Progenitor Cell-Based Therapy of the Human Central Nervous System," *Nature Biotech.* 23:862-871 (2005)). Indeed, applicants' initial study of the efficacy of isolated human glial progenitors revealed no overt effect of cell transplantation on either the condition or fate of the engrafted recipients; despite widespread forebrain myelination, the transplanted mice typically died between 18 and 20 weeks of age, just as did unengrafted shiverers.

The present invention is directed to overcoming these and other deficiencies in the art.

SUMMARY OF THE INVENTION

One aspect of the present invention is directed to a non-human mammal with at least 30% of all of its glial cells in its corpus callosum being human glial cells and/or at least 5% of all of its glial cells in the white matter of its brain and/or brain stem being human glial cells.

Another embodiment of the present invention relates to a method of producing non-human mammals with human glial cells replacing native glial cells in the brain. This method involves providing a population of isolated human glial cells. The population of isolated human glial cells are introduced into multiple locations within the forebrain and/or brain stem of a non-human mammal. A non-human mammal with human glial cells replacing native glial cells in the brain is then recovered.

A further aspect of the present invention pertains to a method of assessing in vivo human glial cell response to injury, stroke, inflammatory stimuli, toxicants, or therapeutic agents. The steps of this method include providing a non-human mammal either with at least 30% of its glial cells in its corpus callosum being human glial cells and/or with at least 5% of its glial cells its brain and brain stem white matter being human glial cells. The non-human mammal is subjected to injury, stroke, inflammatory stimuli, toxicants, or therapeutic agents. As a result, the in vivo human glial cell response to the injury, stroke, inflammatory stimuli, toxicants, or therapeutic agents is assessed.

Another embodiment of the present invention is directed to a method of assessing in vivo response of human myelin to injury, stroke, inflammatory stimuli, myelinotoxic agents, or therapeutic agents. This method is carried out by providing a non-human mammal either with at least 30% of its glial cells in its corpus callosum being human glial cells or with at least 5% of its glial cells its brain and brain stem white matter being human glial cells. The non-human mammal is subjected to injury, stroke, inflammatory stimuli, myelinotoxic agents, or therapeutic agents. As a result, the in vivo human myelin response to the injury, stroke, inflammatory stimuli, myelinotoxic agents, or therapeutic agents is assessed.

In the work corresponding to the present invention, using a newly developed set of approaches to both cell acquisition and transplantation, a far more extensive and higher density cell engraftment was attempted than any previously noted. The aim in doing so was to achieve sufficiently widespread central myelination to influence the phenotype and survival of the recipient animals. To avoid rejection as a complicating variable in these experiments, shiverer mice were crossed with rag2 null immunodeficient mice (Shinkai et al., "RAG2-Deficient Mice Lack Mature Lymphocytes Owing to Inability to Initiate V(D)J Rearrangement," *Cell* 68:855-867 (1992)), thereby generating an immunodeficient line of congenitally hypomyelinated mice in which to assess graft efficacy and effect. Using these double homozygous rag2$^{-/-}$×shiverer$^{shi/shi}$ mice, a multi-site injection protocol, with concurrent bilateral hemispheric and cerebellar cell injections delivered at birth was established. This procedure resulted in widespread donor cell engraftment throughout the neuraxis, with infiltration of the forebrain, brainstem and cerebellum, and ultimately the spinal cord and roots. The engrafted human glial progenitor cells exhibited robust, efficient, and functional myelination, with progressive ensheathment of host axons and restoration of normal nodes of Ranvier and attendant conduction velocities. This ultimately led to the high efficiency myelination of the major intracerebral, ascending and descending tracts, the cranial nerves and intracranial ganglia, and the spinal cord to the thoracolumbar level. Most notably, the implanted animals exhibited a substantial recovery of normal neurological phenotype, such that a fraction were frankly rescued by perinatal transplantation, surviving well over a year until sacrificed for histology, which revealed both a remyelinated—and essentially humanized—central white matter. The neurological recovery and sustained survival of these transplanted mice was in sharp contrast to the fate of their untreated controls, which uniformly died by 5 months of age. Together, these data represent the first outright rescue of a congenital leukodystrophy, or indeed of any hereditary-metabolic disorder, by means of a stem or progenitor cell transplantation. Such results indicate that neonatal glial progenitor cell transplantation may prove an effective means of treating disorders of both hereditary and perinatal hypomyelination.

BRIEF DESCRIPTION OF THE DRAWINGS

FIGS. 1A-B, respectively, show plots of percent survival and seizures per hour versus age in days. In FIG. 1A, Shiverer/rag2$^{-/-}$ mice, either engrafted with human glial progenitor cells (GPCs) at birth (n=26, red), injected with saline (n=29, green), or untreated (n=59, blue) were maintained in small group housing and monitored daily until death. The Kaplan-Meier survival graph, plotting the percentage of each group alive as a function of age in weeks, shows that most mice die between 18 and 20 weeks. However, a fraction of engrafted mice (n=6, or 23.1%) lived substantially longer than any control mouse; 4 survived more than one year, at which point the experiment was terminated. FIG. 1B shows that Shiverer mice uniformly manifested a seizure disorder that was typically apparent by 5 weeks of age, and then worsened between 16-18 weeks. When seizure frequency was scored by video with blinded post hoc assessment, both transplanted and control shiverers were noted to seize frequently during weeks 18-20, corresponding to the time span during which most mice died. However, the seizure incidence among the transplanted shiverers fell thereafter, such that by 47 weeks of age, all surviving mice were seizure-free.

FIGS. 2A-B show serial sagittal images of an engrafted shi/shi×rag2$^{-/-}$ brain, sacrificed at 1 year of age. Each image in FIGS. 2A and 2B represents a montage of 50-100 images at 10×. Each series begins 750 μm lateral to the midline, and continues at 600 μm intervals. FIG. 2A shows human donor cells, immunolabeled in 14 μm cryosections using an anti-human nuclear antibody (hN; red). FIG. 2B shows Alexa 488-labeled myelin basic protein (MBP; green) in sections adjacent or nearly so to their matched sections in FIG. 2A. All major white matter tracts, including those of the corpus callosum, capsules, striatum, fimbria, cerebellum and brainstem heavily express MBP. FIGS. 2C-G are black-and-white images of MBP-immunoreactive fibers in a number of sites which reveal high efficiency axonal myelination; all images of transplanted shi/shi×rag2$^{-/-}$ mice at >1 year post-transplant. In FIG. 2C, the rostral striatum, corpus callosum, and neocortical layers 5 and 6 are shown in sagittal section. FIG. 2D shows higher magnification of FIG. 2C and shows the MBP-defined myelination of individual fibers within the striatum, as well as the larger bundles of corticostriatal and striopallidal fibers. FIG. 2E depicts donor-myelinated MBP$^+$ fibers in a longitudinal section of the cervical spinal cord; dorsal column to the left, central gray to the right. In FIG. 2F, interwoven donor-myelinated fibers of the brainstem, in the pontine base are shown. FIG. 2G shows donor-derived MBP in the conus medullaris; exiting myelinated roots of the cauda equina to the left. Scale: FIGS. 2A-B=2.5 mm; FIG. 2C=200 μm; FIG. 2D=40 μm; FIG. 2E=50 μm; FIG. 2F=60 μm; FIG. 2G=125 μm.

FIGS. 3A-B show both the dense concentration of human donor cells (anti-human nuclear antigen, red) in the trigeminal ganglion (TG), and the concurrent prohibition of donor cell infiltration into the trigeminal nerve (nV), a peripheral nerve. Accordingly, donor-derived myelin (MBP, green) was limited to the ganglion and trigeminal nerve take-off, and did not extend into nV proper. FIG. 3C shows a wider field color composite of FIGS. 3A-B (FIGS. 3A-B correspond to the boxed area of FIG. 3C), further demonstrating that the transplanted GPCs strictly respect the CNS-PNS border. In contrast, FIGS. 3D-E show an adjacent section stained for the peripheral myelin protein P0 (blue), and for either human nuclear antigen (red) or central myelin basic protein (green). The human cells are seen to have stopped at the P0 protein-defined threshold to the PNS. Scale=50 μm.

FIGS. 4E-4F show that transcallosal responses were evoked by electrical stimulation in mice in vivo. FIG. 4E plots the transcallosal conduction velocities obtained from wild-type, rag2$^{-/-}$, shiverer× rag2$^{-/-}$ (shi/rag2), and transplanted shiverer×rag2$^{-/-}$ mice (Tpt), all assessed between 12-13 months after neonatal transplant. FIG. 4F shows the relationship between stimulus intensity and signal amplitude in C3H wild-type mice, rag2$^{-/-}$ mice, shiverer×rag2$^{-/-}$ mice, and transplanted shiverer× rag2$^{-/-}$ mice, respectively.

In FIG. 5A, major white matter regions of the brain, including the corpus callosum, fimbria, optic tract, and both the cerebral and cerebellar peduncles, are already myelinated at 20 weeks. As shown in FIG. 5B, at 35 weeks, the area of dense myelination has expanded into the midbrain and hindbrain. As depicted in FIG. 5C, by a year, myelin was well-distributed, and myelination appeared complete, throughout the forebrain and hindbrain, and includes the lowers layers of neocortex, the colliculi, the pons and medulla, as well as the major corticopontine and corticospinal tracts.

FIG. 5G shows myelin lamellae surrounding resident host axons; FIG. 5H, a higher magnification view of the field indicated in FIG. 5G, reveals the major dense lines within these myelin wraps. FIGS. 5A-C, 2.5 mm; FIGS. 5D-F, 10 μm; FIGS. 5G-H, 1 μm.

FIG. 6E is a parasagittal section including dorsal callosum and overlying cortex of a transplanted shiverer at 20 weeks, showing human donor-derived myelination of callosum, and admixture of host (blue, DAPI) and donor cells (purple, as blue co-labeled with hNA, red). Both myelinated (MBP, green) and unmyelinated (GFAP, scarlet) fibers are evident traversing lower cortical layers. In FIG. 6F, higher magnification section through fimbria of hippocampus, showing myelinated fibers viewed en face, with admixed mouse (blue) and human (purple, representing blue co-labeled with hNA, red) cells. Scale: FIG. 6E, 100 μm; FIG. 6F, 50 μm.

DETAILED DESCRIPTION OF THE INVENTION

Figure 1:
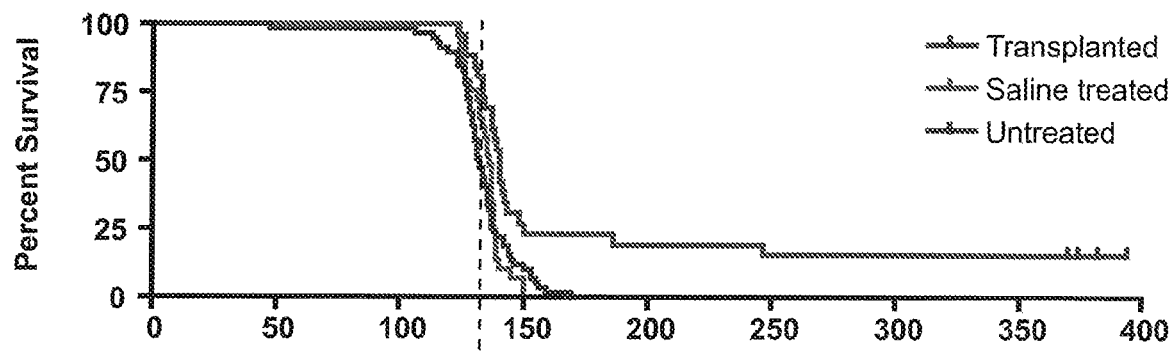
Figure 1:

One aspect of the present invention is directed to a non-human mammal with at least 30% of all of its glial cells in its corpus callosum being human glial cells and/or at least 5% of all of its glial cells in the white matter of its brain and/or brain stem being human glial cells. Preferably, at least 50% (more preferably, at least 70%, and most preferably at least 90%) of all glial cells in the corpus callosum of the non-human mammal are human glial cells. Alternatively, at least 10% (preferably), at least 15% (more preferably), or at least 20% (most preferably) of all glial cells in the white matter of the non-human mammal's brain and/or brain stem are human glial cells. In another embodiment, the white matter is cerebellar white matter and at least 50% of all glial cells in the cerebellar white matter are human glial cells.

The non-human mammal can be any pre-natal, neo-natal, or adult non-human mammal. Any non-human mammal is suitable for carrying out the present invention, including mice, rats, guinea pigs and other small rodents, dogs, cats, sheep, goats, and monkeys. In a preferred embodiment of the present invention, the non-human mammal is a mouse.

It is desirable that the non-human mammal host accepts the human glial cells with little or no adverse immune recognition. Therefore, it is preferred that the non-human mammal is immuno-incompetent, immuno-deficient, or immuno-suppressed.

Immunosuppression can be achieved either through the administration of immunosuppressive drugs such as cyclosporin, sirolimus, or tacrolimus, or through strategies employing locally applied immunosuppressants. Local immunosuppression is disclosed by Gruber, *Transplantation* 54:1-11 (1992), which is hereby incorporated by reference. U.S. Pat. No. 5,026,365 to Rossini, which is hereby incorporated by reference, discloses encapsulation methods also suitable for local immunosuppression.

As an alternative to employing immunosuppression techniques, methods of gene replacement or knockout using homologous recombination, as taught by Smithies et al. *Nature* 317:230-234 (1985), which is hereby incorporated by reference in its entirety, can be applied to donor glial cells for the ablation of major histocompatibility complex (MHC) genes. Donor glial cells lacking MHC expression would allow for the transplantation of an enriched glial cell population across allogeneic, and perhaps even xenogeic, histocompatibility barriers without the need to immunosuppress the recipient. General reviews and citations for the use of recombinant methods to reduce antigenicity of donor cells are also disclosed by Gruber, *Transplantation* 54:1-11 (1992), which is hereby incorporated by reference in its entirety. Exemplary approaches to reduce immunogenicity of transplants by surface modification are disclosed in WO92/04033 to Faustman, which is hereby incorporated by reference in its entirety.

Alternatively, the immunogenicity of the transplanted cells may be reduced by using any non-human mammal host that possesses a genetic mutation rendering it immunodeficient. Exemplary animal models include those having a mutation which disrupts the recombination activating gene 2 (Rag2) (Shinkai et al., *Cell* 68:855-867 (1992), which is hereby incorporated by reference in its entirety) or the Rag1 gene (Mombaerts et al., *Cell* 68:869-877 (1992) and Schultz et al., *Transplantation* 76:1036-42 (2003) which are hereby incorporated by reference in their entirety). Other immunodeficient animal models useful for practicing the present invention include any of the severe combined immunodeficient mice (SCID), having a mutation in the Prkdc gene. Preferred SCID mouse models for use in the present invention include the NOD-SCID, the NOD-SCID-IL2rg, and the NOG (NOD-SCID/γc$^{null}$) mouse models. Additionally, the Nude mouse models, carrying a mutation in the Foxn1 gene are also useful for practicing the present invention.

Another embodiment of the present invention relates to a method of producing non-human mammals with human glial cells replacing native glial cells in the brain. This method involves providing a population of isolated human glial cells. The population of isolated human glial cells are introduced into multiple locations within the forebrain and/or brain stem of a non-human mammal. A non-human mammal with human glial cells replacing native glial cells in the brain is then recovered.

The non-human mammal has the same characteristic as described above.

In accordance with the methods of the present invention, the population of human glial cells to be transplanted into the non-human mammal host animal are preferably bi-potential glial progenitor cells. In one embodiment, the glial progenitor cells can be biased to producing oligodendrocytes. Alternatively, the glial progenitor cells can be biased to producing astrocytes. In a further embodiment of the present invention, the human glial cells to be transplanted into the non-human mammal host animal can be astrocytes.

Glial progenitor cells can be obtained from embryonic, fetal, or adult brain tissue, embryonic stem cells, or induced pluripotential cells. Preferably, the glial progenitor cells are isolated from ventricular and subventricular zones of the brain or from the subcortical white matter.

Glial progenitor cells can be extracted from brain tissue containing a mixed population of cells directly by using the promoter specific separation technique, as described in U.S. Patent Application Nos. 20040029269 and 20030223972 to Goldman, which are hereby incorporated by reference in their entirety. This method involves selecting a promoter which functions specifically in glial progenitor cells, and introducing a nucleic acid encoding a marker protein under the control of said promoter into the mixed population cells. The mixed population of cells is allowed to express the marker protein and the cells expressing the marker protein are separated from the population of cells, with the separated cells being the glial progenitor cells.

Glial specific promoters that can be used for isolating glial progenitor cells from a mixed population of cells include the CNP promoter (Scherer et al., *Neuron* 12:1363-75 (1994), which is hereby incorporated by reference in its entirety), an NCAM promoter (Holst et al., *J. Biol. Chem.* 269:22245-52 (1994), which is hereby incorporated by reference in its entirety), a myelin basic protein promoter (Wrabetz et al., *J. Neurosci. Res.* 36:455-71 (1993), which is hereby incorporated by reference in its entirety), a JC virus minimal core promoter (Krebs et al., *J. Virol.* 69:2434-42 (1995), which is hereby incorporated by reference in its entirety), a myelin-associated glycoprotein promoter (Laszkiewicz et al., "Structural Characterization of Myelin-associated Glycoprotein Gene Core Promoter," *J. Neurosci. Res.* 50(6): 928-36 (1997), which is hereby incorporated by reference in its entirety), or a proteolipid protein promoter (Cook et al., "Regulation of Rodent Myelin Proteolipid Protein Gene Expression," *Neurosci. Lett.* 137(1): 56-60 (1992); Wight et al., "Regulation of Murine Myelin Proteolipid Protein Gene Expression," *J. Neurosci. Res.* 50(6): 917-27 (1997); and Cambi et al., *Neurochem. Res.* 19:1055-60 (1994), which are hereby incorporated by reference in their entirety). See also U.S. Pat. No. 6,245,564 to Goldman et. al., which is hereby incorporated by reference in its entirety.

Alternatively, it may be preferable to isolate the glial progenitor cells by first removing neurons or neural progenitor cells from the mixed cell population. Where neuronal progenitor cells are to be separated from the mixed population of cells, they can be removed based on their surface expression of NCAM, PSA-NCAM, or any other surface moiety specific to neurons or neural progenitor cells. Neurons or neural progenitor cells may also be separated from a mixed population of cells using the promoter based separation technique. Neuron or neural progenitor specific promoters that can be used for separating neural cells from a mixed population of cells include the Tα1 tubulin promoter (Gloster et al., *J. Neurosci.* 14:7319-30 (1994), which is hereby incorporated by reference in its entirety), a Hu promoter (Park et al., "Analysis of Upstream Elements in the HuC Promoter Leads to the Establishment of Transgenic Zebrafish with Fluorescent Neurons," *Dev. Biol.* 227(2): 279-93 (2000), which is hereby incorporated by reference in its entirety), an ELAV promoter (Yao et al., "Neural Specificity of ELAV Expression: Defining a Drosophila Promoter for Directing Expression to the Nervous System," *J. Neurochem.* 63(1): 41-51 (1994), which is hereby incorporated by reference in its entirety), a MAP-1B promoter (Liu et al., *Gene* 171:307-08 (1996), which is hereby incorporated by reference in its entirety), or a GAP-43 promoter. See U.S. Pat. No. 6,245,564 to Goldman et. al., which is hereby incorporated by reference in its entirety.

Having selected a promoter specific for the cell of interest, a nucleic acid molecule encoding a protein marker, preferably a green fluorescent protein under the control of the promoter is introduced into a plurality of cells to be sorted. The isolated nucleic acid molecule encoding a green fluorescent protein can be deoxyribonucleic acid (DNA) or ribonucleic acid (RNA, including messenger RNA or mRNA), genomic, recombinant, or mutant, biologically isolated or synthetic as described in U.S. Patent Application No. 20040029269 to Goldman, which is hereby incorporated by reference in its entirety. Other suitable marker proteins include lacZ/beta-galactosidase or alkaline phosphatase.

Standard techniques are then used to place the nucleic acid molecule encoding the marker protein under the control of the chosen cell specific promoter. Generally, this involves the use of restriction enzymes and ligation.

The resulting construct, which comprises the nucleic acid molecule encoding the marker protein under the control of the selected promoter (itself a nucleic acid molecule) (with other suitable regulatory elements if desired), is then introduced into a plurality of cells which are to be sorted and then sorting. Techniques for introducing the nucleic acid molecules of the construct into the plurality of cells and then sorting the cells are described in U.S. Patent Application No. 20040029269 to Goldman et al., which is hereby incorporated by reference in its entirety.

Once the nucleic acid molecule encoding the marker protein is introduced into a plurality of cells, the promoter which controls expression of the marker protein only functions in the cell of interest. Therefore, the marker protein is only expressed in the cell of interest and those cells can be identified from among the plurality of cells by the expression of the marker protein (e.g. fluorescence of the GFP using any suitable means of fluorescent detection). For GFP, cells may be identified using epifluorescence optics, and can be physically picked up and brought together by Laser Tweezers (Cell Robotics Inc., Albuquerque, N.Mex.). Alternatively, the cells can be separated in bulk through fluorescence activated cell sorting, a method that effectively separates the fluorescent cells from the non-fluorescent cells.

As an alternative to using promoter-based cell sorting to recover glial progenitor cells from the mixed population, an immunoseparation procedure can be utilized. In a positive immunoselection technique, the desired cells (i.e. glial progenitor cells) are isolated based on proteinaceous surface markers naturally present on the progenitor cells. For example, the surface marker A2B5 is an initially expressed early marker. See Nunes et al., "Identification and Isolation of Multipotential Neural Progenitor Cells from the Adult Human White Matter," *Soc. Neurosci. Abstr.* (2001), which is hereby incorporated by reference. Using an antibody specific to that marker, glial progenitor cells can be separated from a mixed population of cell types.

Alternatively, or in combination with the positive immunoselection method described above, a mixed cell population can be depleted of undesirable cell types, leaving the desired cell population. This method involves separating cells based on proteinaceous surface markers that are specific to cell populations other than the glial progenitor cells (i.e. neuronal cells, endothelial cells, etc.) and retaining the glial progenitor cell population.

Cell specific antibodies for immunoseparation techniques can be labeled with a fluorescent, biotin, or hapten label to facilitate separation of cells to which they bind. Alternatively, the antibodies can be attached to paramagnetic beads so that cells which bind to the beads through the attached antibodies can be recovered by a biomagnetic separation process. Any other suitable method for cell separation known in the art, including attachment to and disattachment from solid phase (i.e. immunopanning), is also within the scope of the present invention The glial progenitor cells can be transplanted bilaterally into multiple sites of the non-mammal host animal. Methods for transplanting nerve tissues and cells into host brains are described by Bjorklund and Stenevi (eds), Neural Grafting in the Mammalian CNS, Ch. 3-8, Elsevier, Amsterdam (1985); U.S. Pat. No. 5,082,670 to Gage et al.; and U.S. Pat. No. 6,497,872 to Weiss et al., which are hereby incorporated by reference in their entirety. Typical procedures include intraparenchymal, intracallosal, intraventricular, intrathecal and intravenous transplantation.

Intraparenchymal transplantation is achieved by injection or deposition of tissue within the host brain so as to be apposed to the brain parenchyma at the time of transplantation. The two main procedures for intraparenchymal transplantation are: 1) injecting the donor cells within the host brain parenchyma or 2) preparing a cavity by surgical means to expose the host brain parenchyma and then depositing the graft into the cavity (Bjorklund and Stenevi (eds), *Neural Grafting in the Mammalian CNS*, Ch. 3, Elsevier, Amsterdam (1985), which is hereby incorporated by reference in its entirety). Both methods provide parenchymal apposition between the donor cells and host brain tissue at the time of grafting, and both facilitate anatomical integration between the graft and host brain tissue. This is of importance if it is required that the donor cells become an integral part of the host brain and survive for the life of the host.

Glial progenitor cells can also be delivered intracallosally as described in U.S. Patent Application No. 20030223972 to Goldman. In a preferred embodiment of the present invention, glial progenitor cells are delivered directly to the forebrain subcortex, specifically into the anterior and posterior anlagen of the corpus callosum. Glial progenitor cells can also be delivered to the cerebellar peduncle white matter to gain access to the major cerebellar and brainstem tracts. Glial progenitor cells can also be delivered to the spinal cord.

Alternatively, the cells may be placed in a ventricle, e.g. a cerebral ventricle. Grafting cells in the ventricle may be accomplished by injection of the donor cells or by growing the cells in a substrate such as 30% collagen to form a plug of solid tissue which may then be implanted into the ventricle to prevent dislocation of the graft cells. For subdural grafting, the cells may be injected around the surface of the brain after making a slit in the dura.

In another embodiment of the present invention, transplantation of the glial progenitor cells can be carried out using intravenous or intrathecal administration as described by Pluchino et al., "Injection of Adult Neurospheres Induces Recovery in a Chronic Model of Multiple Sclerosis," *Nature* 422(6933):678-94 (2003), which is hereby incorporated by reference in its entirety.

Injections into selected regions of the host brain may be made by drilling a hole and piercing the dura to permit the needle of a microsyringe to be inserted. The cell suspension is drawn up into the syringe and administered to anesthetized recipients. Multiple injections may be made using this procedure. The microsyringe is preferably mounted in a stereotaxic frame and three dimensional stereotaxic coordinates are selected for placing the needle into the desired location of the brain or spinal cord.

In one embodiment of the present invention the non-human host mammal is myelin-depleted when the human glial progenitor cells are introduced. In another embodiment, the non-human host mammal has a storage disorder affecting neurons, or a storage disorder affecting astrocytes, or a storage disorder affecting oligodendrocytes. In a further embodiment, the non-human host mammal is a wild-type or normal animal.

Once the human glial progenitor cells are introduced, the mammal is permitted to age, causing the mammal to produce more human glial cells as it ages. In addition, the mammal undergoes myelination as it ages Survival of the human glial progenitor cells in the host mammal can be examined using various non-invasive scans such as computerized axial tomography (CAT scan or CT scan), nuclear magnetic resonance or magnetic resonance imaging (NMR or MRI) or more preferably positron emission tomography (PET) scans. Post-mortem examination of cell survival and integration can be done by histological examination of various brain regions macroscopically, or more preferably using microscopy. Cells can be labeled with any stain visible under light or electron microscopic conditions, more particularly with stains which are specific for host glia cells. Particularly useful are antibodies which specifically identify the human donor cells, including the mouse anti-human nuclei, clone 235-1, and antibodies which demonstrate myelin production by the donor cells, including anti-myelin basic protein antibodies. Transplanted cells can also be identified by prior incorporation of tracer dyes such as rhodamine- or fluorescein-labeled microspheres, fast blue, bisbenzamide or retrovirally introduced histochemical markers such as the lac Z gene which produces beta galactosidase.

A further aspect of the present invention pertains to a method of assessing in vivo human glial cell response to injury, stroke, inflammatory stimuli, toxicants, or therapeutic agents. The steps of this method include providing a non-human mammal either with at least 30% of its glial cells in its corpus callosum being human glial cells and/or with at least 5% of its glial cells its brain and brain stem white matter being human glial cells. The non-human mammal is subjected to injury, stroke, inflammatory stimuli, toxicants, or therapeutic agents. As a result of the subjecting, the in vivo human glial cell response to the injury, stroke, inflammatory stimuli, toxicants, or therapeutic agents is assessed.

The non-human mammal has the same characteristic as described above.

The non-human mammal can be used as an animal model for traumatic or ischemic injury. As a result, the in vivo human glial cell response to traumatic or ischemic injury can be assessed.

The non-human mammal can also be an animal model for stroke which permits the in vivo human glial cell response to stroke be assessed.

The non-human mammal can alternatively be an animal model for inflammatory stimuli. As a result, the in vivo human glial cell response to inflammatory stimuli may be assessed. The inflammatory stimuli to be assessed include, but are not limited to, multiple sclerosis, transverse myelitis, and experimental allergic encephalomyelitis.

The non-human mammal may also be subjected to a toxicant or a therapeutic agent. Therapeutic agents which can be assessed include, but are not limited to agents which may perturb glial or neuronal function, agents for non-CNS targets, agents for the treatment of epilepsy, and agents for treatment of multiple sclerosis.

The step of assessing may involve determining the behavior or fate of the human glial cells using a metric selected from the group consisting of morphology, immunophenotype, transcriptionally-regulated reporters, gene expression profiles, mitotic rate, mitotic fraction, metabolic rate, mitochondrial function, oxidative state, telomerase activity, myelin structure or relative volume (G-ratio), apoptotic index, or net cell survival.

When assessing involves examining cellular morphology, the assessment can include measurements of the cell size, fiber outgrowth, length, complexity, or anchorage. Such measurements can be carried out using standard neurohistological techniques known in the art. Typically, such analyses include examining various sections of brain tissue that have been processed according to the histological method employed and labeled with one or more cell specific or nucleic acid markers to aid in examination and measurements. Measurements can be performed using brightfield or fluorescent microscopy, confocal microscopy, or electron microscopy depending on the particular endpoint to be measured.

When the assessing step involves examining immunophenotype, such as an increase or decrease in cell specific gene expression, immunocytochemical, immunoblotting, flow cytometry, or fluorescence-activated cell sorting techniques can be used to measure immunophenotype. The specific cellular protein, RNA, or DNA to be assessed (i.e. receptor, enzyme, signaling protein, etc.) will depend on the endpoint being investigated (i.e. stroke, injury, therapeutic agent, toxicant).

Likewise, when the assessing step includes the examination of gene expression profiles to determine an increase or decrease in cell specific gene expression, microarrays, real-time PCR, or protein expression profiling techniques readily known in the art can also be employed. U.S. Patent Application No. US20050176626 to Goldman et al., which is hereby incorporated by reference in its entirety, describes methods for assessing gene expression in human white matter progenitor cells and provides a comprehensive list of gene targets, which can be adapted for use in the methods of the present invention.

If the step of assessing includes examining transcriptionally-regulated reporters, promoter/enhancer-driven reporters in enzymatic or fluorescent form are utilized.

When the assessing step includes examining mitochondrial function, any one of a variety of assays known in the art to examine mitochondrial function or integrity can be employed. For example, mitochondrial metabolic activity can be measured using methods described by Springer et al., "A Rapid and Sensitive Assay for Measuring Mitochondrial Metabolic Activity in Isolated Neural Tissue," *Brain Research Protocol* 2(4):259-263 (1998), which is hereby incorporated by reference in its entirety can be utilized. Alternatively, the rate of oxygen consumption as an indicator of mitochondrial function can be measured as described by Will et al., "Analysis of Mitochondrial Function Using Phosphorescent Oxygen-Sensitive Probe," *Nature Protocols* 1:2563-72 (2007), which is hereby incorporated by reference in its entirety, can also be employed. Additionally, there are various commercially available dyes and stains, which are specific for visualizing and measuring mitochondria viability (Invitrogen, Carlsbad, Calif.). Alternatively, mitochondrial specific gene expression can be examined as a measure of mitochondrial function.

If the assessing step includes examining apoptosis, it is preferable that a variety apoptotic endpoints are examined. Such endpoints include an assessment of the nucleus, specifically, fragmentation of chromatin, degradation of the nuclear envelope and nuclear blebbing. Several nucleic acid stains are known in the art and are commercially available to facilitate the detection of DNA integrity as a measure of apoptosis by fluorescence imaging or flow cytometry. Other indices of apoptosis to be measured include cellular permeability, caspase enzyme activity (Slee et al., *Cell* Death Differ 6:1067-74 (1999); Linca L F, *Immunol Cell Biol* 76:1-19 (1998), which are hereby incorporated by reference in their entireties), externalization of phosphatidylserine (van Engeland et al., *Cytometry* 31:1-9 (1998), which is hereby incorporated by reference in its entirety), disruption of mitochondria, including changes in the membrane potential and alteration to the oxidation-reduction potential (Finkel E., *Science* 292:624-626 (2001); Brenner et al., *Science* 289:1150-1151 (2000); Desagher et al., *Trends Cell Biol* 10:369-377 (2000), which are all hereby incorporated by reference in there entirety) and significant alterations in levels of intracellular ions or the ratio of ATP to ADP.

Another embodiment of the present invention is directed to a method of assessing in vivo response of human myelin to injury, stroke, inflammatory stimuli, myelinotoxic agents, or therapeutic agents. This method is carried out by providing a non-human mammal either with at least 30% of its glial cells in its corpus callosum being human glial cells or with at least 5% of its glial cells its brain and brain stem white matter being human glial cells. The non-human mammal is subjected to injury, stroke, inflammatory stimuli, myelinotoxic agents, or therapeutic agents. As a result of the subjecting step, the in vivo human myelin response to the injury, stroke, inflammatory stimuli, myelinotoxic agents, or therapeutic agents is assessed.

In carrying out this aspect of the present application, the non-human mammal has the same characteristics, model utilities, and uses as described above.

In addition, the non-human mammal can be subjected to a myelinotoxic agent and the therapeutic agent may be selected from the group consisting of an agent to perturb glial or neuronal function, an agent to perturb neural transmission, an agent for non-CNS targets, an agent for treatment of epilepsy, an agent for treatment of multiple sclerosis, and an agent to promote remyelination.

Further, the step of assessing can be carried out in substantially the manner noted above.

EXAMPLES

Example 1

Cell Extraction

Fetal oligodendrocyte progenitor cells ("OPCs") were extracted from second trimester human fetuses (19 to 22 weeks gestational age, g.a.), obtained at abortion as described (Windrem et al., "Fetal and Adult Human Oligodendrocyte Progenitor Cell Isolates Myelinate the Congenitally Dysmyelinated Brain," *Nature Medicine* 10:93-97 (2004), which is hereby incorporated by reference in its entirety). The forebrain ventricular/ subventricular zones were rapidly dissected from the remaining brain parenchyma, the samples chilled on ice, and the minced samples then dissociated using papain/DNAse as described (Keyoung et al., "Specific Identification, Selection and Extraction of Neural Stem Cells from the Fetal Human Brain," *Nature Biotechnology* 19:843-850 (2001), which is hereby incorporated by reference in its entirety), always within 3 hours of extraction. The dissociates were then maintained overnight in minimal media of DMEM/F12/N1 with 20 ng/ml FGF. A total of 5 tissue samples (1 at 19 wks g.a., 1 at 20 wks, 3 at 22 wks) were used for this study, all from chromosomally normal fetal donors. All samples were obtained with consent under approved protocols of the University of Rochester, Cornell/New York Presbyterian Hospital, and Albert Einstein College of Medicine/Jacoby Hospital Institutional Review Boards.

Example 2

Cell Sorting

Sorted glial progenitor cells were isolated from dissociated tissue using a dual immunomagnetic sorting strategy. On the day after dissociation the cells were incubated with mouse anti-PSA-NCAM (Chemicon) at 1:100. then washed and labeled with microbead-tagged rat anti-mouse IgM (Miltenyi Biotech), and removed by MACS depletion. The remaining PSA-NCAM$^-$ cells were next incubated 1:1 with MAb A2B5 supernatant (clone 105; ATCC, Manassas, Va.), for 20 minutes, then washed and labeled with microbead-tagged rat anti-mouse IgM (Miltenyi Biotech). All incubations were done on ice (Keyoung et al., "Specific Identification, Selection and Extraction of Neural Stem Cells from the Fetal Human Brain," *Nature Biotechnology* 19:843-850 (2001) and Roy et al., "In Vitro Neurogenesis by Progenitor Cells Isolated from the Adult Human Hippocampus," *Nat Med* 6:271-7. (2000), which are hereby incorporated by reference in their entirety). Magnetic separation of A2B5$^+$ cells (MACS; Miltenyi) was then performed, as described (Nunes et al., "Identification and Isolation of Multipotential Neural Progenitor Cells from the Subcortical White Matter of the Adult Human Brain," *Nature Medicine* 9:439-447 (2003), which is hereby incorporated by reference in its entirety). The bound cells were then eluted, yielding a highly enriched population of A2B5$^+$/PSA-NCAM$^-$ cells. After sorting, the cells were maintained in vitro for 1-2 days in DMEM/F12/N1 with 20 ng/ml bFGF, then frozen and stored under liquid nitrogen, at $2\times10^6$ cells/ml in 7% DMSO/93% FBS.

Example 3

Transplantation and Husbandry

Homozygous shiverers were crossed to homozygous rag2 null immunodeficient mice (Shinkai et al., "RAG2-Deficient Mice Lack Mature Lymphocytes Owing to Inability to Initiate V(D)J Rearrangement," *Cell* 68:855-867 (1992), which is hereby incorporated by reference in its entirety), to generate a line of shi/shi×rag2$^{-/-}$ myelin-deficient, immunodeficient mice. Newborn pups of this line were transplanted within a day of birth, using a total of 300,000 donor cells dispersed over 5 injection sites. The pups were first cryoanesthetized for cell delivery. $5\times10^4$ donor cells in 0.5 µl HBSS were then injected at each of 4 locations in the forebrain subcortex, specifically into the anterior and posterior anlagen of the corpus callosum bilaterally. These injections were delivered to a depth of 1.0 to 1.2 mm ventrally, depending on the weight/size of the pup (which varied from 1-1.5 g). A fifth injection of $10^5$ cells in 1 µl was delivered into the cerebellar peduncle dorsally, to gain access to the major cerebellar and dorsal brainstem tracts. All cells were injected through pulled glass pipettes, inserted directly through the skull into the presumptive target sites. The pups were then returned to their mother, until weaning at 21 days; at that point, each litter was moved to separate enriched housing. After weaning, mice were checked at least twice daily. Mice that died from immediate surgical complications or before weaning (2 saline-injected and 1 glial progenitor cell-transplanted) were excluded from the experiment. Typically as of 130 days of age, mice in all groups began to die. They were checked several times daily, and if found so moribund as to be unable to right themselves upon being moved, they were given barbiturate anesthesia, then perfusion-fixed with HBSS followed by 4% paraformaldehyde. When mice were instead found dead, their brains were removed and post-fixed for 2 hrs in cold paraformaldehyde.

Example 4

Survival Analysis and Statistics

Kaplan-Meier analysis was used to assess the different survivals of transplanted and control mice, as described (Hosmer et al., "Applied Survival Analysis," (John Wiley and Sons, New York, 1999), which is hereby incorporated by reference in its entirety). No difference in survival was observed between saline-injected and untreated mice, so the two populations were combined as a single control population for the Kaplan-Meier comparison with GPC-implanted mice.

Analyses of variance (ANOVA) were performed using GraphPad Prism (v4.0c for Macintosh; GraphPad Software, San Diego, Calif.).

Human cells were identified by immunolabeling with mouse anti-human nuclei, clone 235-1 at 1:100 (MAB1281, Millipore, Billerica, Mass.). Myelin basic protein was labeled with rat anti-MBP at 1:25 (Ab7349, Abcam, Cambridge Mass.), and axons with mouse anti-neurofilament cocktail at 1:1000 (SMI-311 and -312, Covance, Princeton, N.J.). Monoclonal antibodies against Caspr, Nav1.6 and Kv1.2 were used at 1:600, 1:200, and 1:200, respectively, and were obtained from NeuroMab (Davis, Calif.). Rabbit anti-Caspr and anti-βIV spectrin were generously provided by Dr. Matthew Rasband (Baylor), while rabbit anti-Caspr2 was obtained from Millipore. Rabbit anti-olig2 was obtained form Abcam (Ab33427) and used at 1:1,500. Alexa Fluor secondary antibodies, goat anti-mouse, rat, and rabbit 488, 568, 594 and 647 were used at 1:400 (Invitrogen, Carlsbad, Calif.).

Example 5

Myelinated Axon Counts

Uniform random sagittal sections of the cervical spinal cord, and coronal sections of the corpus callosum, were both selected for neurofilament and MBP staining; in the spinal cord samples, the most medial sections were analyzed with respect to the percentage of myelinated host axons. A 1 μm stack of 10 superimposed optical slices taken at 0.1 μm intervals (Olympus FluoView 300) was made for each of 3 fields of view in the dorsal columns, beginning rostrally and progressing caudally. Three parallel, equidistant lines were laid over the images perpendicular to the axons. Axons were scored at intersections with the lines as either myelinated (closely apposed to MBP on both sides) or unmyelinated. This procedure was then repeated for the coronally-cut samples of corpus callosum.

Example 6

Proportionate Representation of Donor Cells

The percentage of human cells in the recipient white matter was assessed as a function of time after transplantation. Randomly initiated, uniformly sampled sagittal sections of the brains were labeled for human nuclei and DAPI (Vector Labs). 4-6 sections (depending on the persistence of the structure in the selected range of sections) of the corpus callosum, fimbria, and cerebellar white matter were counted, with data entry and reconstruction using BioQuant. All human nuclei and DAPI-labeled cells in the white matter regions of these 14 μm sections were counted.

Example 7

Electron Microscopy

The four mice that survived over a year were perfused transcardially with HBSS, followed by 4% paraformaldehyde with 0.25% glutaraldehyde and 6% sucrose in phosphate buffer (sucrose-PB). One hemisphere of each brain and longitudinal half of each spinal cord were post-fixed in 2% paraformaldehyde, 2.5% glutaraldehyde in sucrose-PB for electron microscopy; the other half of each brain and spinal cord were post-fixed in 4% paraformaldehyde in sucrose-PB for immunohistochemistry. Tissue samples used for electron microscopy were osmicated, dehydrated in ethanol, and embedded in Epon. Ultrathin sectioning was performed using a PowerTome X Ultramicrotome (RMC products by Boeckeler, Tucson, Ariz.). The ultrathin sections were collected on formvar-coated copper one-hole grids and contrasted with lead citrate and uranyl acetate, then examined in a JEOL 100CX transmission electron microscope.

Example 8

Seizure Counts

Mice were placed in a sterilized Plexiglass cage with a camera embedded in the ceiling (Pheno Typer, Noldus, Wageningen, the Netherlands) and left undisturbed overnight while their movements were recorded by infra-red light. Six non-overlapping half-hour video segments were randomly selected from each 8 hour videotape, excluding the first 3 hour segment so as to diminish any effects of the novel environment. Two segments for each mouse scored were assigned to each of 3 observers, blinded as to the mouse's age and treatment. The observers recorded and timed each mouse's seizures, which were defined as such when the mouse fell to its side and assumed a rigid, stereotypically tonic posture, typically complicated by clonic flexion-extension of the trunk and limbs. A seizure was timed as ending when the mouse first moved to right itself. The number of seizures per hour, and the total ictal time per hour, were thereby scored.

Example 9

Transcallosal Transmission

Mice were anesthetized with katamine (60 mg/kg, i.p.) and xylazine (10 mg/kg, i.p.), intubated through a tracheotomy and ventilated with a ventilator (SAR-830, CWE, Inc., Ardmore, Pa.). A femoral artery was catheterized for monitoring mean artery blood pressure and blood gases, and body temperature was maintained at 37° C. by a warming blanket (Harvard Apparatus, Holliston, Mass.). Mice were secured with a custom-made metal frame that was glued to the skull with acrylic cement. Two burr holes, each 3 mm in diameter, were made bilaterally, centered 1-2 mm posterior to bregma and 2-3 mm from the midline. The dura was removed and agarose (0.75% in saline) was poured into the craniotomy sites, which were then closed with a 0.17 mm thick glass coverslip. The head frame was then attached to a second frame that was coupled to the microscope stage. Glass micropipettes filled with 2M NaCl solution were then inserted to a depth of 200 μm into the right cortex, at 1.5 mm posterior to bregma and 2.5 mm from the midline, for recording the local field potentials (LFPs) generated by transcallosal electric stimulation. Electrical stimulation (100 μs at 10-1000 μA, via an ISO-Flex isolator controlled by a Master-8 programmer; AMPI, Israel) was applied using a bipolar electrode inserted at the same coordinates in the contralateral (left) hemisphere. Evoked LFPs were recorded by a multiClamp 700A amplifier, filtered at a cutoff frequency of 1 kHz, and sampled at an interval of 200 μs by a pCLAMP 9.2 program and DigiData 1332A interface (Axon Instruments Inc.). The same electrode was used to continuously monitor the electrocorticogram (ECoG). ECoG was recorded continuously by a multiClamp 700A Amplifier (Axon) with a low frequency filter at 1 Hz and high frequency filter at 100 Hz (51, 52), and a pCLAMP 9.2 program and DigiData 1332A interface (Axon) with an interval of 200 μs. The amplitude of stimulus-evoked transcallosal response was then calculated as the difference between the peak and baseline, whereby the baseline was defined as the average potential measured during the 20 ms before the stimulation was delivered. The velocity of transcallosal response was calculated, together with the latency of the response and the distance between the stimulating and recording electrodes. The response latency was defined as the difference between the stimulus start and the peak. Two recordings of the transcallosal responses to electric stimulation (0.10 ms, 0.01-0.10 mA) were obtained from each animal.

Example 10

Engrafted Shiverer Mice Exhibited Substantially Prolonged Survival

Newborn double-homozygous shiverer (shi/shi)×rag2$^{-/-}$ immunodeficient mice were implanted with either 300,000 human glial progenitor cells (GPCs) (n=26), with PBS vehicle control (n=29), or with nothing (n=59). Cells were delivered at 5 sites, including the anterior and posterior corpus callosa bilaterally, and the presumptive cerebellar peduncle as a single midline injection; PBS controls received equal volume injections at each site, while the no-injection controls were not injected. The mice were then returned to their mothers and allowed to develop normally, with weaning at 21 days and small group housing thereafter. All mice were observed to undergo progressive neurological deterioration, typically first manifested by a progressive truncal instability worse upon ambulation, followed with marked hindlimb weakness by 14-16 weeks of age, and seizures beginning at 4-6 weeks but rapidly increasing in frequency by 18-19 weeks. Thus, by 18 weeks, all mice exhibited markedly impaired forward ambulation, and frequent episodes of sustained seizures. Over a range of 130-150 days postnatally, all of the 29 PBS-treated and 53 untreated control shiverer mice died, with median and mean (±SE) survivals of 135.0±1.4 and 132.4±2.1 days, respectively.

In sharp contrast, of the 26 implanted mice, 20 died during this period, but 6 (23.1%) survived. Whereas the average survival of the untreated controls approximated 130 days, and none of the 82 total control mice survived to 150 days, these 6 implanted mice survived over 160 days, and 4 appeared to have been frankly rescued, surviving over a year before being sacrificed for analysis. Remarkably, these mice exhibited overtly improved neurological function, with decreased seizure incidence and improved mobility and self-care. Indeed, transplanted mice surviving beyond 190 days exhibited apparent treatment-dependent cure, with sustained survival over a year, accompanied by a virtually complete recovery of normal neurological phenotype. As a result, the engrafted mice as a group exhibited significantly prolonged survival: Kaplan-Meier analysis (Hosmer et al., "Applied Survival Analysis," (John Wiley and Sons, New York, 1999), which is hereby incorporated by reference in its entirety) confirmed that the treatment-associated improvement in survival was statistically significant, and profoundly so (p=0.0003; hazard ratio=0.4718 (95% CI=0.30-0.70) (FIG. 1A).

Example 11

Transplantation was Associated with Neurological Improvement and Diminished Seizures The rescued mice exhibited substantial resolution of their neurological deficits. Shiverer mice typically exhibit truncal instability and marked intention tremor, evident within weeks of birth, which becomes complicated by a progressive hindlimb weakness, and multimodal sensory and perceptual deficits that include blindness, such that by 18-19 weeks of age they are severely impaired. In addition, they manifest a progressively worsening seizure disorder, often succumbing to status epilepticus—if they do not die first of being unable to care for themselves. Given the substantially longer survivals noted in a fraction of the transplanted shiverers, applicants asked what the behavioral concomitants were to transplantation, as a function of time after cell delivery. Applicants were especially interested in any discernible differences in the behavior or neurological status of shiverer mice that were rescued by neonatal GPC transplant, relative to transplanted littermates that nonetheless died. It was noted that all of the shiverers, both transplanted and controls, deteriorated identically over the first several months after birth and transplantation. Indeed, up to 130 days, the point at which mice typically began to die in number, little difference was observed in the behaviors of transplanted relative to untransplanted shiverer mice. However, those mice that survived the period spanning 130-150 days postnatally, exhibited noticeable improvement in their neurological exams thereafter, frankly manifest by 7-8 months of age as diminished frequency of seizures and improved ambulation, with more forward motion and less retropulsion or freezing. Over the several months thereafter, the transplanted mice incrementally improved, regaining normal fluidity in ambulation, normal voluntary explorative behavior, and less truncal intention tremor. All 5 mice surviving to at least 35 weeks of age were substantially normal by that point and thereafter in terms of their grossly assessable neurological function, save for a coarse axial intention tremor, manifesting as a wobble on forward ambulation.

Since the death of most mice at 130-150 days of age was coincident with the period of sharply increasing seizure activity, the frequency and duration of seizures in both untreated and transplanted shi/shi×rag2 nulls, as a function of age, was assessed; special attention was paid to the incidence of seizures in transplanted mice that were rescued by transplant, compared to their treated counterparts that nonetheless succumbed. It was found that the first seizures of shiverer mice—typically characterized by absence-like episodes of tonic akinesia, followed by a rapid evolution to brief tonic-clonic events—appeared by 35-42 days of age (FIG. 1B). At approximately 120 days, the incidence of seizures was noted to substantially increase, in both treated and untreated animals alike. Over the period spanning 120-140 days, the seizure incidence of each group increased, yielding frequent seizures every hour; these ictal events progressed to sustained periods of status epilepticus, often associated by death. However, in those animals that survived this period to enjoy long-term survival, seizure incidence fell dramatically, such that no seizure activity whatsoever was observed at 12 months (p<0.0001 by 1 way ANOVA, separately comparing 12 month transplanted animal seizure incidence to that of 4 month transplanted and control shiverers). Thus, perinatal glial progenitor cell transplantation was associated with markedly diminished seizure activity in those shi/shi×rag2 null mice that were rescued by perinatal transplantation, such that by a year, none manifested any residual seizure activity whatsoever, while otherwise exhibiting virtually complete neurological recovery. Although these data do not yet allow one to causally attribute the sustained survival of these transplanted shiverers to the diminution of their seizure activity, the increased incidence of seizures coincident with the period during which most shiverers die, coupled with the diminished seizure incidence of those transplanted survivors that go on to survive (compare FIG. 1B to FIG. 1A), suggests that improved seizure control contributes to the sustained viability of the long-surviving transplant recipients.

Example 12

Perinatal Grafts of Human Glial Progenitors Yield Widespread and Dense Host Myelination To assess the terminal distribution of donor cells and robustness of myelination in the transplanted animals, and to compare the extent of donor cell dispersal and myelination between short- and long-term survivors, the latter were ultimately sacrificed at 13 months of age, after assessment of their transcallosal conduction velocities and seizure frequency. The brains and spinal cords of these mice were then analyzed in terms of donor cell distribution and density, myelin production and the proportion of myelinated axons, nodal architecture and reconstitution, and ultrastructural metrics including myelinated axons, and myelin G-ratios. Each of these metrics was then compared to those obtained from transplanted mice that had died earlier, as well as to unimplanted shiverer controls, as well as to wild-type, normally myelinated rag2 null mice.

Figure 2:
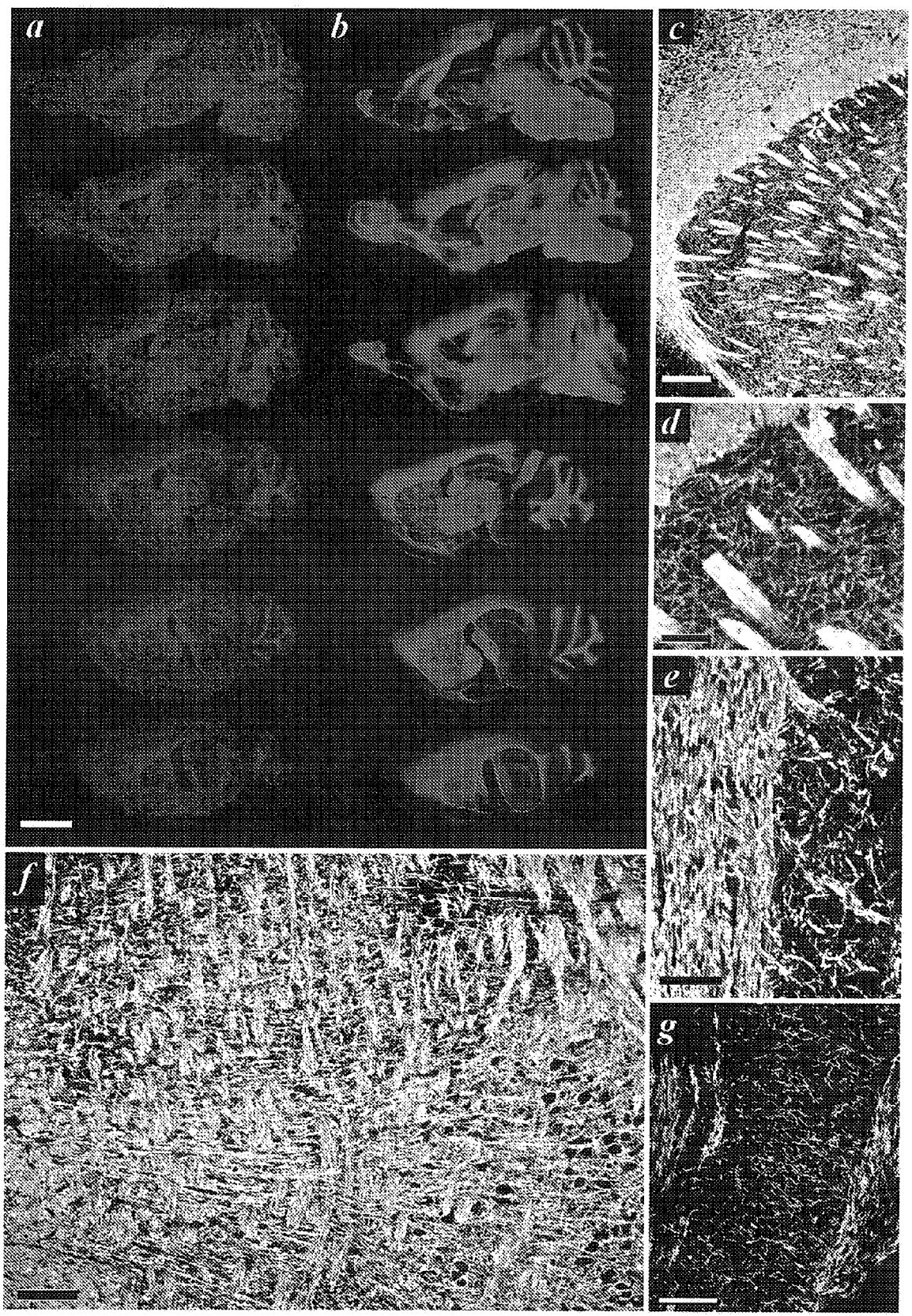
Figure 3:
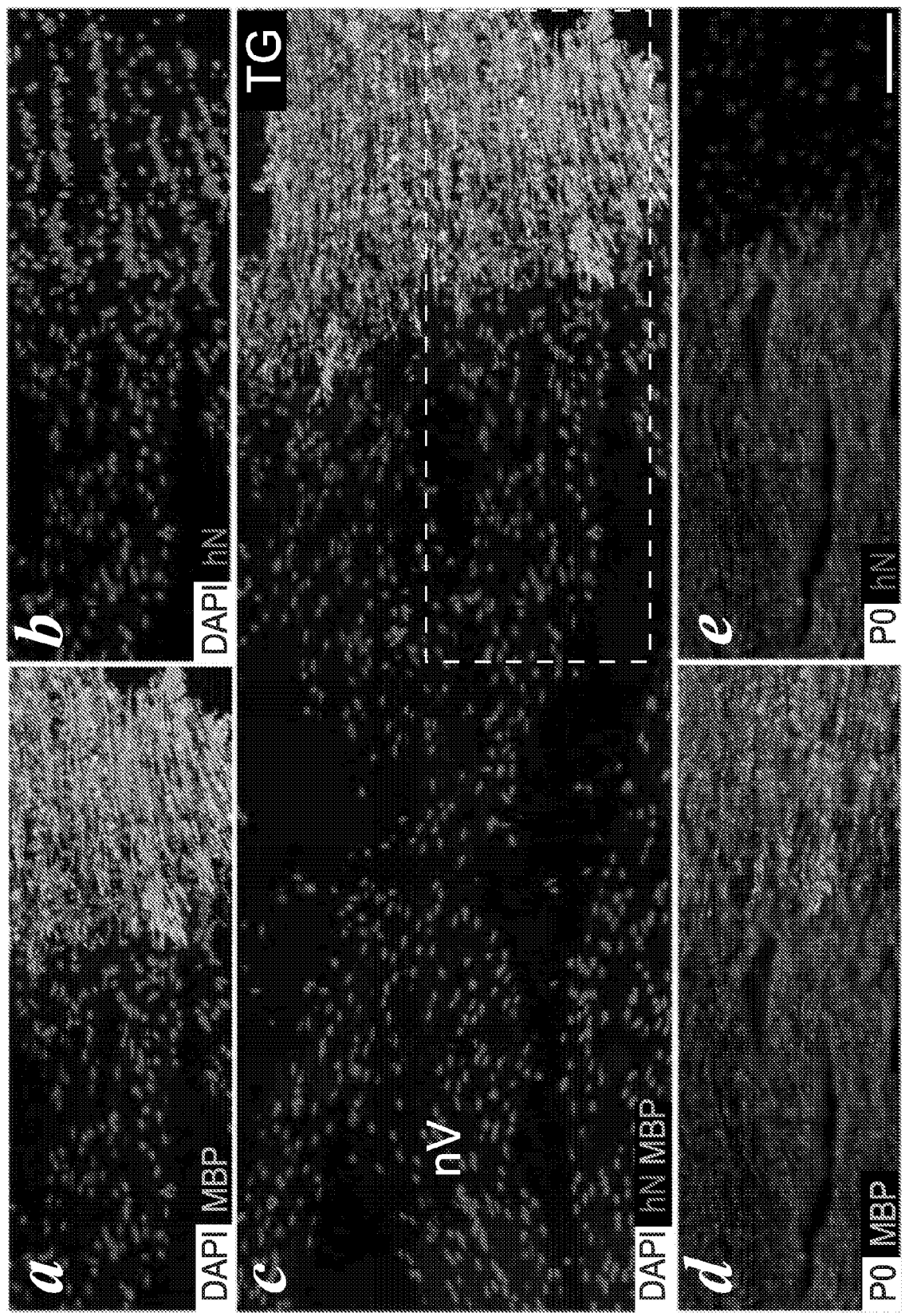
FIGS. 3A-E show that transplanted mice exhibited robust myelination throughout the entire CNS neuraxis by 9 months of age, that included not only the brain, brainstem, cerebellum and spinal cord, but also the cranial nerves, ganglia, and both cranial and spinal roots (see FIGS. 2 and 4). Of note, the invasion of human glial progenitor cells, all derived from the fetal forebrain, was sharply delimited to the CNS, with no invasion whatsoever of the peripheral nerves beyond the root take-offs.

These histological data supported the compelling nature of the survival data. Human donor cell engraftment was extraordinarily extensive, with essentially whole neuraxis penetration and colonization by the human donor OPCs (FIG. 2A). High donor cell densities were observed throughout the forebrain, cerebellum, brainstem, and cervical spinal cord, diminishing only at the level of the thoracolumbar cord, yet increasing again in the sacral cord and conus medullaris. The pattern of myelination, as indicated by MBP expression, reflected this widespread engraftment, with equally widespread and dense myelination (FIGS. 2B-F), including not only all major central white matter tracts, but also structures as distant and diverse as the cranial ganglia, optic chiasm and conus medullaris (e.g., FIG. 2G). These long-term survivors, whose neurological exams had largely normalized by 9 months of age, exhibited essentially complete myelination of the brain, brainstem, and cerebellum, with substantial myelination of the optic nerves (FIG. 2B), spinal cord (FIG. 2E), and spinal roots (FIG. 2G), as well as of the cranial roots and ganglia (FIGS. 3A-C). In regards to the latter, the cessation of donor glial progenitor cell migration at the border of CNS and PNS was striking, such that donor-derived myelination occurred up to, but not beyond, the transition points demarcating central ganglia and roots from peripheral nerve (FIGS. 3A-E). The resultant densities and patterns of donor cell dispersal resulted in the virtually complete chimerization of the murine hosts' central nervous systems, which thereby acquired a largely humanized white matter. Three-dimensional reconstructions confirmed that both the pattern and density of donor-derived myelination in the brains of transplanted shiverers approximated that of wild-type, normal mice.

Example 13

Xenografted Shiverer Brains Exhibit Restored Nodes of Ranvier

Applicants next asked if donor cell-derived myelination of shiverer axons was accompanied by the acquisition of normal nodes of Ranvier and paranodal structure (FIGS. 4A-D). Using high-resolution confocal imaging of the corpus callosa, cervical spinal cords, and optic nerves of implanted shiverers killed at 35 or 52 weeks of age, the distribution pattern of the paranodal and juxtaparanodal proteins Caspr and the $K_v1.2$ voltage-gated potassium channel, respectively, was assessed. The contiguous interaction of these proteins characterizes the normal node of Ranvier (Schafer et al., "Glial Regulation of the Axonal Membrane at Nodes of Ranvier," Curr. Opinion in Neurobiology 16:508-514 (2006) and Rasband et al., "Developmental Clustering of Ion Channels At and Near the Node of Ranvier," Dev. Biol. 236:5-16 (2001), which are hereby incorporated by reference in their entirety). These potassium channels are assembled at—and functionally define—the juxtaparanodes in myelinated axons, but they are broadly and nonspecifically expressed in unmyelinated fibers (Rasband et al., "Developmental Clustering of Ion Channels At and Near the Node of Ranvier," Dev. Biol. 236:5-16 (2001), which is hereby incorporated by reference in its entirety). In addition, the axonal expression and compartmentalization of $Na_v1.6$ fast sodium channels, which are typically sequestered at nodes of Ranvier in intact myelinated axons, but dispersed broadly along unmyelinated or dysmyelinated fibers, was determined. Similarly, applicants immunostained for βIV-spectrin, which couples to ankyrin to organize fast sodium channels at the node of Ranvier, and hence typically coincides with nodal $Nav1.6$ expression (Schafer et al., "Glial Regulation of the Axonal Membrane at Nodes of Ranvier," Curr. Opinion in Neurobiology 16:508-514 (2006); Yang et al., "βIV Spectrin is Recruited to Axon Initial Segments and Nodes of Ranvier by AnkyrinG," J Cell Biol 176:509-19 (2007); and Sherman et al., "Mechanisms of Axon Ensheathment and Myelin Growth," Nature Rev. Neurosci. 6:683-690 (2005), which are hereby incorporated by reference in their entirety).

Using these complementary nodal markers, an essentially normal organization of the nodes of Ranvier in transplanted mice was identified, which was indistinguishable from that of wild-type mice. Caspr and $K_v1$. were expressed in organized paranodal and juxtaparanodal apposition, with an expression pattern that contrasted sharply with the grossly uncoordinated pattern of diffuse Caspr and $K_v1.2$ immunolabeling that was evident in the untransplanted controls (FIGS. 4A-D). Similarly, both $Na_v1.6$ (FIGS. 4A'-D') and βIV-spectrin (FIGS. 4A"-4D") clearly identified nodes of Ranvier in the transplanted shi/shi mice, flanked by Caspr defining the paranodes, whereas their untransplanted controls showed no such sequestration of either $Na_v1.6$ or βIV-spectrin expression. Together, these observations suggest that despite interspecies chimerization, the glio-axonal interactions of human GPC-derived oligodendrocytes with host mouse axons were functionally appropriate. More broadly, they indicate that GPC-derived oligodendrocytes are able to communicate effectively with host axons, organizing structurally appropriate nodes of Ranvier while sequestering fast sodium channels within the nodes, and thereby myelinating their axonal substrates both effectively and appropriately.

Example 14

Transcallosal Conduction Velocities are Restored in Xenografted Shiverer Brains

In light of the apparent histological reconstitution of normal myelin, applicants next asked if donor OPC-derived myelin was sufficient in both extent and functional competence to restore the conduction speed of newly myelinated central axons. To this end, the conduction velocity across the corpus callosum in a sample of 4 long-surviving transplanted shiverer mice, between 12 and 13 months after neonatal xenograft was evaluated. The transcallosal nerve conduction velocities were determined by recording response amplitudes and times from depth electrodes placed at several sites in the corpus callosa of each of these mice, after contralateral stimulation at symmetric sites during open craniotomy. Equal numbers of age-matched wild-type (congenic C3h) mice and rag2-null controls were assessed identically, as was a necessarily younger (4 months) sample of untransplanted shiverer× rag2 null mice. Of note, as this was a terminal procedure, these animals, all of which had exhibited not only sustained survival but also a substantial restoration of normal neurological function, were sacrificed after measurement of their transcallosal conduction velocities, thus ending the survival study in which they were subjects.

Figure 4:
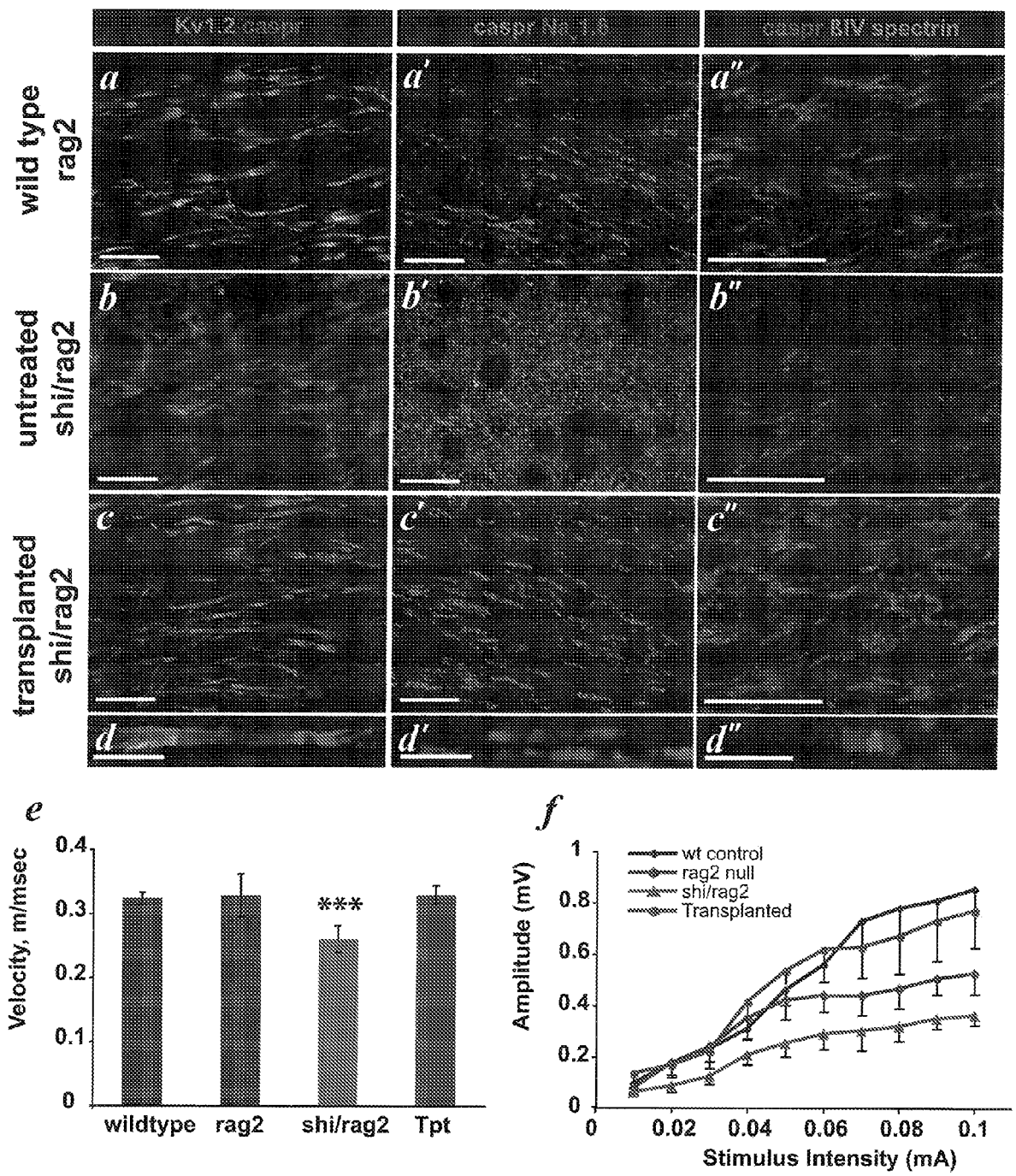
FIGS. 4A-F show the expression patterns of several antigens characteristic of nodes of Ranvier, including nodal ($Na_v1.6$, $\beta IV$-spectrin), paranodal (Caspr) and juxtaparanodal ($K_v1.2$) proteins, which were investigated in the spinal cord (FIGS. 4A-D and 4A'-D') and optic nerves (FIGS. 4A"-4D") of normally-myelinated wild-type (rag2$^{-/-}$) mice (FIGS. 4A-A"), and compared to the corresponding expression patterns in the optic nerves of both untreated (FIGS. 4B-B"), and transplanted (FIGS. 4C-4C" and FIGS. 4D-D") shiverer×rag2$^{-/-}$ mice. The nodal architecture of the transplanted shiverers was indistinguishable from that of wild-type controls for every antigen tested; both exhibited the sodium channel and spectrin clustering, flanked by the paranodal Caspr and juxtaparanodal $K_v1.2$, of mature nodes. The nodal integrity of the transplanted shiverers (FIGS. 4C-C" and FIGS. 4D-D") contrasted sharply to the disorganized and indistinct antigen expression patterns of the untreated mice (FIGS. 4B-B"), in which neither nodal channel clustering nor paranodal Caspr sequestration was noted.

Applicants found that whereas the normal Fvb wild-type (n=3) and rag2 null mice (n=4) exhibited conduction velocities of 0.324±0.01 and 0.328±0.03 m/sec, respectively, the shiverer×rag2 mice (n=4) exhibited substantially slower conduction, at 0.260±0.02 m/sec (FIG. 4E). In contrast, transplanted shiverer×rag2 mice, tested just prior to sacrifice 12-13 months post-transplant (n=3), had an average conduction velocity of 0.330±0.01 m/sec. Repeated measures ANOVA with post hoc Boneferroni t tests revealed a significant treatment effect (F=35.15 [3, 9 df]), such that callosal conduction by the transplanted mice was significantly faster than untransplanted shiverer×rag2$^{-/-}$ mice (p<0.001), and indistinguishable from that of normally myelinated Fvb wild-type and rag2 null mice. The more rapid transcallosal conduction exhibited by the transplanted mice was sustained across stimulus intensities, and thus appeared to represent improved conduction across a wide spectrum of fiber diameters (FIG. 4F). Thus, neonatal transplantation of human oligodendrocyte progenitor cells ("OPCs") yielded sufficient myelin, in terms of both of its density and physiological competence, to restore normal inter-hemispheric conduction velocity to a major central tract, the corpus callosum.

Example 15

Myelination and Axonal Ensheathment were Progressive Over Time

Applicants had had previously established that the dispersal of donor cells following neonatal implantation of human GPCs was relatively rapid, with the terminal distributions of engrafted progenitors occurring within 4-8 weeks of neonatal administration, and myelination proceeding over the several months thereafter (Windrem et al., "Fetal and Adult Human Oligodendrocyte Progenitor Cell Isolates Myelinate the Congenitally Dysmyelinated Brain," *Nature Medicine* 10:93-97 (2004), which is hereby incorporated by reference in its entirety). In the present study, given the extended survival of mice transplanted in both brain and brainstem, applicants were able to assess the later progression of myelination in the graft recipients. Applicants asked whether myelination continued to progress even after extended survival had been achieved. To that end, the brains of transplanted shiverers at 18-20 (n=10), 27 (n=1), 35 (n=1) and 52-56 (n=4) weeks of age were examined and the distribution pattern and densities of human donor cells, as well as of donor-derived myelin, in these recipient brains were assessed. (The 20 week-olds had died natural deaths despite their extensive donor cell engraftment, while the 52-56 week-olds were long-survivors, which had been killed to allow histological analysis. The deaths of the 27 and 35 week-old mice—natural and accidental deaths, respectively—provided informative, if singular, intermediate time points.).

Figure 5:
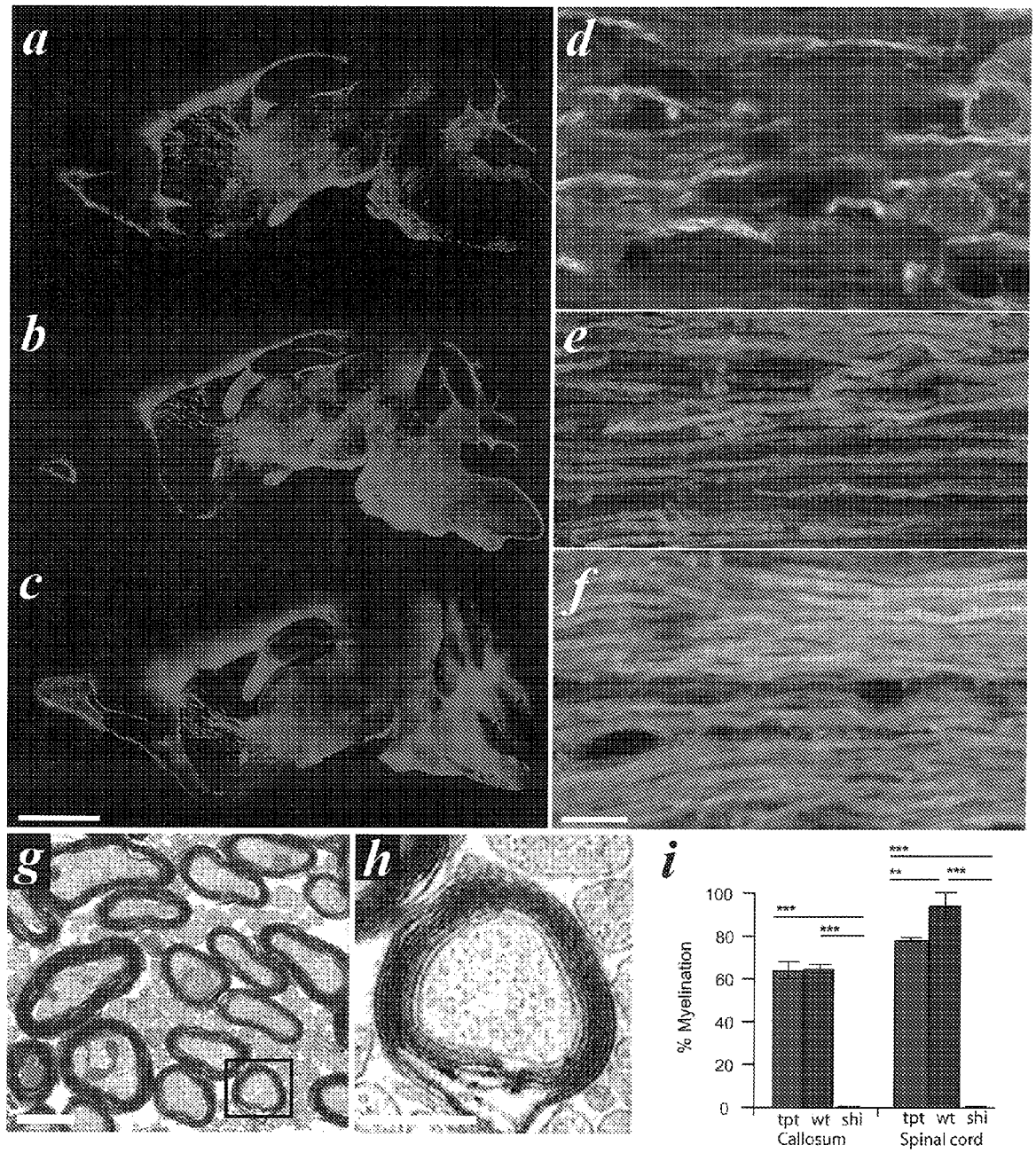
FIGS. 5A-C show sagittal sections of hGPC-implanted mice immunolabeled for MBP (green) at 20 weeks (FIG. 5A), 35 weeks (FIG. 5B), and 52 weeks (FIG. 5C).
FIGS. 5D-F, corresponding to confocal optical sections of transplanted shiverer mouse corpus callosum taken at 20 (FIG. 5D), 35 (FIG. 5E), and 52 (FIG. 5F) weeks, immunolabeled for neurofilament (red) and MBP (green), reveal the progressive increase in axonal ensheathment with time.
FIGS. 5G-H are electron micrographs of the same corpus callosum as that viewed in FIG. 5F at 52 weeks.
FIG. 5I plots the proportion of MBP-ensheathed axons, as determined by confocal analysis, in the corpus callosa (CC) and cervical corticospinal tracts of the spinal cord (SC) in 1 year-old implanted and wt/rag2 null mice. At both sites, most axons in the transplant recipients were ensheathed by MBP-defined myelin. In contrast, no ensheathment was noted in their untreated counterparts. Scale.

Applicants found that while cerebral and cerebellar myelination, as followed by MBP expression, were both substantial and geographically widespread at 20 weeks, both the density and distribution of MBP expression in the brainstem and cervical spinal cord were more extensive at 35 weeks than 20, and much more so at 52-56 weeks (FIGS. 5A-C and 5D-F). In particular, the 52-56 week-old transplanted mice exhibited essentially complete myelination of the brainstem (FIG. 5C and FIG. 2B), whereas the 20 week-olds still exhibited a number of regions of relative hypomyelination relative to wild-type controls (FIG. 5A). The areas of relatively delayed myelination included the ventral long tracts of the brainstem, as well as the brainstem tegmentum and intrinsic internuclear tracts, all of which were more extensively myelinated at 52 weeks of age than at earlier time-points. By scoring the proportion of ensheathed host axons in confocal optical sections immunostained for MBP and neurofilament, it was found that by 52 weeks, 78.0±4.8% of axons in the cervical corticospinal tract at the cervico-medullary junction were myelinated (FIG. 5I), only a marginally smaller proportion than that observed in wild-types (93.9±0.9%). At that same timepoint, the proportion of myelinated axons in both the corpus callosum and corticospinal tract of the transplanted animals was indistinguishable from that of their wild-type controls; each exceeded 60% (FIG. 5I). Transmission electron microscopy (TEM) was next used to validate the criteria by which applicants defined myelin-ensheathed axons in the confocal analysis. TEM of both the corpus callosum and cervical corticospinal tract of 12-13 month-old transplanted shiverers established that the majority of axons in these regions manifested ultrastructurally normal myelination (FIGS. 5G-H), thereby confirming that axons which appeared successfully ensheathed in confocal optical sections were indeed so.

Figure 6:
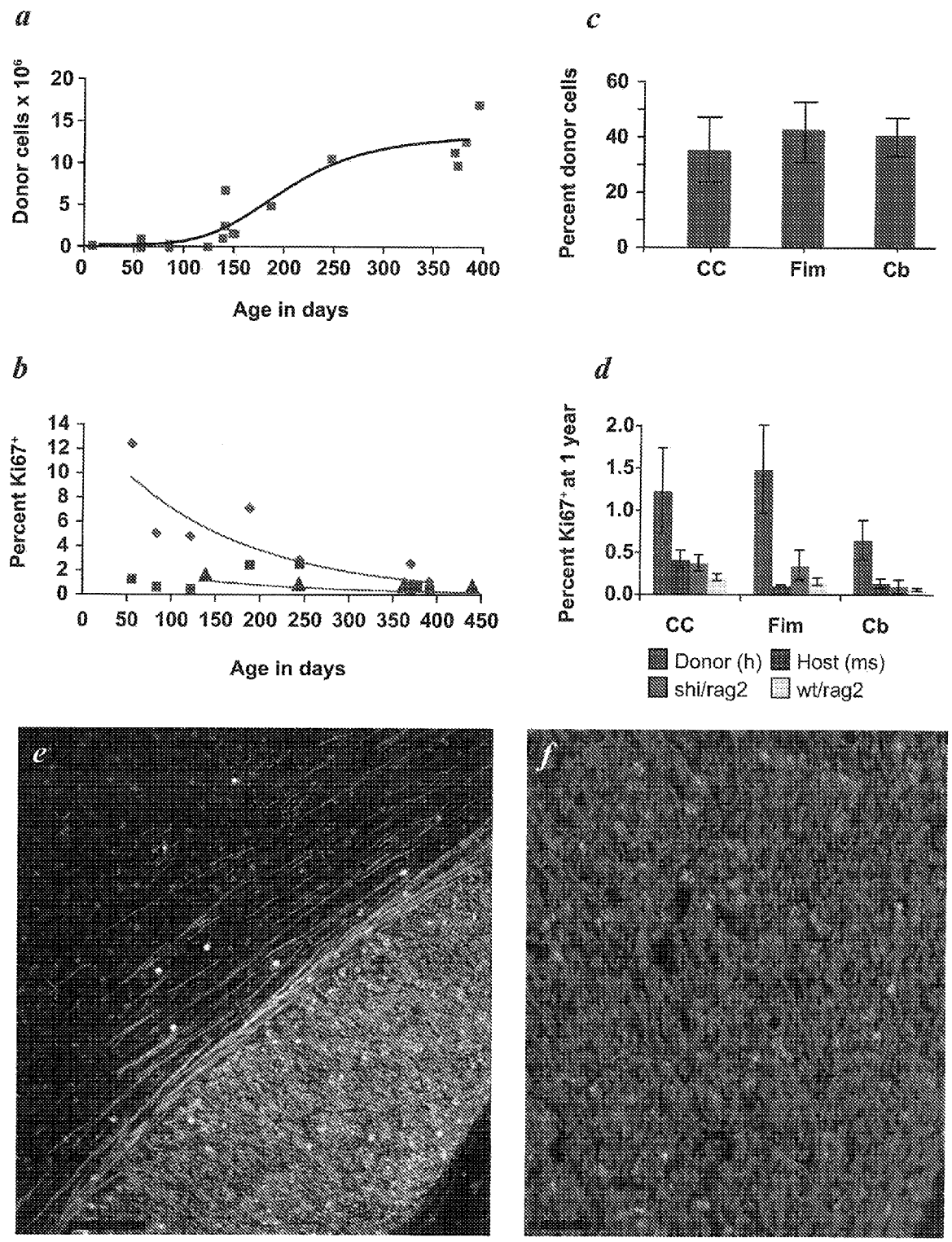
FIG. 6A shows perinatally transplanted human GPCs increase in number asymptotically over the course of a year. From an initial dose of 300,000 on postnatal day 1, the cells increase to an average of 12 million/brain by one year post transplantation ($y=-9,898,000+733,632x+(-5709)^2$; $r^2=0.83$).
As shown in FIG. 6B, by one year, donor cells comprised over 40% of all cells in the fimbria and cerebellar white matter, and over a third in the corpus callosum. Since the total cell count includes host vascular cells and microglia, the human donor-derived cells appeared to comprise a net majority of all glial cells by that stage.
In FIG. 6C, over the year after implantation, the rate of human GPC proliferation in white matter declined exponentially (red; $y=14.013e^{-0.0475x}$; $r^2=0.79$). At 8 weeks, 12.35% of human GPCs in the mouse corpus callosum are Ki67 positive, but by one year, an average of 1.22% are Ki67 positive. From 5 to 12 months, the percentage of Ki67+ mouse cells in the corpus callosum of untreated rag2 null mice also declined exponentially, but beginning at a lower rate (purple; $y=2.9154e^{-0.0497x}$; $r^2=0.83$). The Ki67+ percentages of endogenous mouse cells in the same sections of transplanted mice from which the hGPC percentages were obtained, however, do not follow a pattern of exponential decline (blue; $y=1.3684e-0.02x$ $r^2=0.1855$).
As shown in FIG. 6D, at one year, the percentage of hGPCs in white matter that are Ki67+ (red) exceeds that of the endogenous mouse cells in the same mice (blue), as well as that of untreated rag2 null mice (yellow), and that of 4 month old untreated shiverer/rag2 homozygotes (green) in corpus callosum, fimbria and cerebellum.
FIGS. 6E-F show that progressive myelination (MBP, green) of mouse axons (neurofilament, in red) was attended by chimerization of the recipient white matter, such that by 20 weeks, host cells (DAPI, blue) are exceeded by human donor cells (human nuclear antigen, hNA, purple, as blue co-labeled with hNA, red).
Figure 7:
FIG. 7 shows a heterozygote twitcher×rag1 null mouse, phenotypically normal for myelin, implanted neonatally with fetal human glial progenitor cells. Upon sacrifice over a year later, widespread dispersal of human donor-derived glia was observed throughout both gray and white matter compartments of both brain and brainstem. These normally myelinated recipients exhibited a substantially greater degree of gray matter compartmentalization of the injected donor cells than did congenitally hypomyelinated hosts.

The progressive myelination of transplanted shiverers did not appear to be a function of the rate or kinetics of donor cell dispersal, in that the topography of donor cells at 35 weeks did not differ substantially from that observed at 52 weeks. Nonetheless, the local densities of donor-derived cells did appear to rise over time; this rise was asymptotic (FIG. 6A), which appeared to reflect the fall in mitotic competence of the donor cell pool following their initial expansion in the first half-year or so after transplantation (FIG. 6B). These data suggest that long after human donor cells achieve their destinations, myelinogenesis and axonal ensheathment continue to progress slowly, ultimately achieving the myelination of the recipient neuraxis only after a protracted period of postnatal maturation; this may reflect the incremental engagement of local axons by single oligodendrocytes, as the latter mature and expand their individual domains of myelin ensheathment, adding axons to their ensheathed cohort one at a time over a period of many months.

Example 16

Long-Term Survival was Associated with Humanization of the Recipient White Matter The selective expansion of the human glial population in the shiverer mouse white matter appears to be at least in part a product of the more sustained proliferation of the transplanted human GPCs (FIGS. 6B and 6D), which as derived from the late second trimester fetal subventricular zone ("SVZ"), would be expected to have continued actively dividing for at least another 9-12 months, assuming cell-autonomous regulation of expansion potential. Accordingly, when the number of all human cells in the recipient mouse brains were plotted, as a function of time, it was found that the initial dose of 300,000 cells/recipient had expanded to an average of 12 million human donor glia by 12-14 months in the long-term survivors (FIG. 6A). When the incidence of Ki67$^+$ cells was assessed in three sample regions—the corpus callosum, fimbria, and cerebellar white matter—the fraction of mitotic human donor cells was found to be much higher than that of the local host cells, both perinatally and for many months thereafter; only at a year after engraftment was the Ki67$^+$ fraction of human donor cells observed to fall below 2% (FIG. 6B). Even then, the fraction of Ki67$^+$ human glia remained higher than the corresponding proportion of Ki67$^+$ mouse cells, in both the transplanted hosts, and in the rag2 wild-type or shi/shi×rag2$^{-/-}$ mouse controls (F=12.42 [3, 2 df] by 2-way ANOVA permuting cell type and region; p<0.05 for each comparison, by Boneferroni post hoc t tests) (FIG. 6D). Ultimately though, despite the preferential expansion of the human donor cell pool, its relative mitotic quiescence was achieved by a year after transplantation, according to the approximate time course by which normal human GPCs attenuate their expansion in situ. Importantly in this regard, no evidence of heterotopic foci, anaplasia, or neoplastic transformation was ever noted in over 100 transplanted mice serially examined.

These data indicate that donor human GPCs exhibit more robust and sustained mitotic expansion than their host murine counterparts after transplantation, and that over time, this results in the relative humanization of the recipient white matter. Indeed, quantification of the human donor cell complement revealed that in 4 long-surviving transplanted mice sacrificed at 12-14 months, at least a third of all cells in the corpus callosum, fimbria, and cerebellar white matter were of human origin (35.3±11.8%, 42.9±10.9%, and 40.8±6.9%, respectively) (FIG. 6C). In 3 of the 4, over 40% of all cells in each of these white matter regions were human, and in the densest engraftment among these, that of a mouse sacrificed at 13 months, 54.6% of all cells in its callosum were human. Since just under a third of all cells in the shiverer white matter are non-glial—these include microglia, endothelial cells, and pericytes—it was estimated that at least 80% of all callosal glial cells in this "best-case" mouse were of human origin by a year after engraftment; more broadly, over half of all callosal glia were human in each of the long-surviving transplanted mice assessed.

In these experiments, highly-enriched isolates of human glial progenitor cells were delivered into neonatal shiverer× rag2 null (shi/shi×rag2$^{-/-}$) immunodeficient and myelin-deficient mice, using a multifocal delivery strategy that achieved both widespread and dense donor cell engraftment throughout the recipient CNS. Injection sites were chosen so as to permit contiguous infiltration of migrating donor cells into all major brain, brainstem and spinal white matter tracts, without hindrance from intervening gray matter structures, which may delimit the migration and sustained multilineage competence of engrafted glial progenitor cells (Windrem et al., "Progenitor Cells Derived from the Adult Human Subcortical White Matter Disperse and Differentiate as Oligodendrocytes Within Demyelinated Lesions of the Rat Brain," *J. Neurosci Res* 69:966-975 (2002), which is hereby incorporated by reference in its entirety). By this strategy, the complete, whole neuraxis myelination of the engrafted hosts; in a fraction of these animals was achieved. This resulted in the effective rescue of this otherwise lethal phenotype. These mice exhibited essentially complete myelination of the brain, brainstem, and cerebellum, with substantial myelination of the optic nerves, cranial roots and ganglia, spinal cord, and spinal roots, that was associated with clinical rescue, as reflected by both sustained survival and substantially restored functional competence, the latter as manifested both electrophysiologically and behaviorally.

This transplant-associated reduction in both morbidity and mortality was accompanied by the acquisition of normal nodes of Ranvier and paranodal structure, a restitution of transcallosal conduction velocity, ultrastructurally normal and complete myelination of the overwhelming majority of axons, and a restoration of a substantially normal neurological phenotype. These transplants were also attended by a virtually complete chimerization of the recipient central nervous systems, such that the surviving recipients, and in particular the long-term survivors, developed a largely humanized white matter. Donor cell expansion occurred in an asymptotic fashion, such that chimerization evolved over the 8-9 months after transplantation, with progressive myelination reflecting ongoing axonal ensheathment as much as persistent cell expansion.

Interestingly, the progressive chimerization of the host white matter with admixed human donor cells was attended by a significant loss of both host glial progenitor cells and oligodendroglia. Whether the competitive strength of the human donor cells was the result of more effective axonal interactions by myelinogenic donor cells relative to non-myelinogenic host progenitors, or rather reflected the selective mitotic expansion of the human donor cells in the postnatal murine environment, or even the selective geographic displacement of the host cells by their donor-derived counterparts, is unclear; it seems likely that each of these factors contributed to the marked competitive advantage of the human donor cells. Yet setting aside the nature of this donor-host competition, the degree of the resultant humanization was remarkable: By 13 months of age, over a third of all cells, and the majority of the glial cells within the recipient callosa, fimbria, cerebellar white matter, and cervical spinal cords—indeed, in every region quantified—were human. Moreover, of the recipient axons in these regions, >60% were successfully ensheathed by donor oligodendrocytes; the nodal architecture of the resultant chimerized brains was thus established by human myelin-associated proteins. As a result, multifocal neonatal delivery of human glial progenitor cells to myelin-deficient immunodeficient mice—intended initially as a proof-of-principle of a promising therapeutic approach—has also provided us mice with largely humanized white matter (FIGS. 6E-F), in which the responses of human glial oligodendrocytes and astrocytes to injury and disease may now be observed in real-time, in vivo. This may prove an invaluable experimental model going forward, quite apart from the value of somatic chimerization via progenitor cell allografts as a potential therapeutic approach in the dysmyelinating disorders.

Several reports have noted the potential utility of neural stem or progenitor cell grafts in alleviating both neuronal and oligodendrocytic pathology in animal models of the congenital leukodystrophies, on the basis of their providing wild-type enzymes to animals suffering specific enzymatic deficiencies (Snyder et al., "Neural Progenitor Cell Engraftment Corrects Lysosomal Storage Throughout the MPS VII Mouse Brain," *Nature* 374:367-70 (1995) and Lee et al., "Stem Cells Act Through Multiple Mechanisms to Benefit Mice with Neurodegenerative Metabolic Disease," *Nature Medicine* 13:439-447 (2007), which are hereby incorporated by reference in their entirety). Yet no cell-based treatment of any experimental model of a congenital leukodystrophy, whether hypomyelinative or demyelinative in the setting of a storage disorder, has ever proven sufficient to rescue the underlying phenotype. In particular, no prior treatment of either shiverer mice, or any other congenitally dysmyelinated animal model of a pediatric leukodystrophy, has ever yielded significant survival or long-term functional benefit to the treated recipients. Nonetheless, although the above results suggest the feasibility of an outright rescue of the disease phenotype, it is important to note that only a minority of the transplanted mice so benefited. A major challenge going forward is thus to better define the critical sites that need to be rapidly myelinated to avoid death, and hence allow progressive myelination to ultimately assuage disease progression. The above results suggest that early myelination of the brainstem, and an early transplant-associated diminution in seizure activity, are both associated with clinical rescue; as such, future studies may combine antiepileptic treatment with more posteriorly biased progenitor grafts, as a potential means of improving the likelihood of clinical rescue. These caveats aside, the above results indicate that perinatal transplantation of human glial progenitor cells may be sufficient to rescue a congenital lethal hypomyelination. The sustained viability and restored functional competence of these animals augers well for the potential utility of this approach in the treatment of precociously apparent leukodystrophies, in particular those hypomyelinating disorders manifesting neonatally, such as Pelizaeus-Merzbacher disease (PMD) (Powers, J., "The Leukodystrophies: Overview and Classification in Myelin Biology and Disorders," Vol. 2 (ed. Lazzarini, R. A.) 663-690 (Elsevier Academic Press, San Diego, 2004); Nave et al., "Models of Pelizaeus-Merzbacher Disease in the Myelin Biology and Disorders," Vol. 2 (ed. Lazzarini, R.) 1125-43 (Elsevier Academic, San Diego, 2004); and Garbern et al., "Prenatal Diagnosis of Pelizaeus-Merzbacher Disease," *Prenat. Diagn.* 22:1033-35 (2002), which are hereby incorporated by reference in their entirety). Indeed, the pathological similarity of PMD, an X-linked misexpression of proteolipid protein, to the periventricular leukomalacia of cerebral palsy (Deguchi et al., "Characteristic Neuropathology of Leukomalacia in Extremely Low Birth Weight Infants," *Pediatr Neurol* 16:296-300 (1997); Rezaie et al., "Periventricular Leukomalacia, Inflammation and White Matter Lesions Within the Developing Nervous System," *Neuropathology* 22:106-32 (2002); and Volpe, J. J., "Neurobiology of Periventricular Leukomalacia in the Premature Infant," *Pediatr Res.* 50:553-62 (2001), which are hereby incorporated by reference in their entirety), suggests the potential applicability of this glial progenitor cell-based treatment strategy to a wide range of both hereditary and ischemic (Back et al., "Late Oligodendrocyte Progenitors Coincide with the Developmental Window of Vulnerability for Human Perinatal White Matter Injury," *J Neurosci* 21:1302-12. (2001), which is hereby incorporated by reference in its entirety) childhood disorders of myelin.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A non-human mammal with at least 30% of all of its glial cells in its corpus callosum being human glial cells and/or at least 5% of all of its glial cells in the white matter of its brain and/or brain stem being human glial cells.

2. The non-human mammal according to claim 1, wherein the mammal is pre-natal.

3. The non-human mammal according to claim 1, wherein the mammal is neo-natal.

4. The non-human mammal according to claim 1, wherein the mammal is an adult.

5. The non-human mammal according to claim 1, wherein the mammal is a mouse.

6. The non-human mammal according to claim 1, wherein the mammal is immuno-incompetent, immuno-deficient, or immuno-suppressed.

7. The non-human mammal according to claim 1, wherein at least 10% of all of the glial cells in the white matter of the mammal's brain and/or brain stem are human glial cells.

8. The non-human mammal according to claim 7, wherein at least 15% of all of the glial cells in the white matter of the mammal's brain and/or brain stem are human glial cells.

9. The non-human mammal according to claim 7, wherein the white matter is cerebellar white matter and at least 50% of all glial cells in the cerebellar white matter are human glial cells.

10. The non-human mammal according to claim 1, wherein at least 50% of all of the glial cells in the corpus callosum of the mammal are human glial cells.

11. The non-human mammal according to claim 10, wherein at least 70% of all of the glial cells in the corpus callosum of the mammal are human glial cells.

12. A method of producing non-human mammals with human glial cells replacing native glial cells in the brain, said method comprising:
    providing a population of isolated human glial cells;
    introducing the population of isolated human glial cells into multiple locations within the forebrain and/or brain stem of a non-human mammal; and
    recovering a non-human mammal with human glial cells replacing native glial cells in the brain.

13. The method according to claim 12 wherein the population of isolated human glial cells is a population of human glial progenitor cells.

14. The method according to claim 12, wherein at least 30% of the glial cells in the recovered non-human mammal's corpus callosum are human glial cells.

15. The method according to claim 12, wherein at least 5% of the glial cells in the recovered non-human mammal's white matter of its brain and brain stem are human glial cells.

16. The method according to claim 12, wherein the mammal is pre-natal during said introducing.

17. The method according to claim 12, wherein the mammal is neo-natal during said introducing.

18. The method according to claim 12, wherein the mammal is an adult.

19. The method according to claim 12, wherein the mammal is a mouse.

20. The method according to claim 12, wherein the mammal is immuno-incompetent, immuno-deficient, or immuno-suppressed.

21. The method according to claim 12, wherein the mammal is myelin depleted during said introducing.

22. The method according to claim 12 further comprising:
    permitting the mammal to age after said introducing, whereby the mammal produces more human oligodendrocytes as it ages.

23. The method according to claim 22, wherein the mammal undergoes myelination as it ages.

24. The method according to claim 12, wherein the human glial cells are human oligodendrocyte progenitor cells.

25. A method of assessing in vivo human glial cell response to injury, stroke, inflammatory stimuli, toxicants, or therapeutic agents, said method comprising:
    providing a non-human mammal either with at least 30% of its glial cells in its corpus callosum being human glial cells and/or with at least 5% of its glial cells its brain and brain stem white matter being human glial cells;
    subjecting the non-human mammal to injury, stroke, inflammatory stimuli, toxicants, or therapeutic agents; and
    assessing, as a result of said subjecting, the in vivo human glial cell response to the injury, stroke, inflammatory stimuli, toxicants, or therapeutic agents.

26. The method according to claim 25, wherein the mammal is an animal model for traumatic or ischemic injury, whereby the in vivo human glial cell response to traumatic or ischemic injury is assessed.

27. The method according to claim 25, wherein the mammal is an animal model for stroke, whereby the in vivo human glial cell response to stroke is assessed.

28. The method according to claim 25, wherein the mammal is an animal model for inflammatory stimuli, whereby the in vivo human glial cell response to inflammatory stimuli is assessed.

29. The method according to claim 28, wherein said inflammatory stimuli is selected from the group consisting of multiple sclerosis, transverse myelitis, and experimental allergic encephalomyelitis.

30. The method according to claim 25, wherein the non-human mammal is subjected to a toxicant.

31. The method according to claim 25, wherein the non-human mammal is subjected to a therapeutic agent.

32. The method according to claim 31, wherein the therapeutic agent is selected from the group consisting of an agent to perturb glial or neuronal function, an agent for non-CNS targets, an agent for treatment of epilepsy, and an agent for treatment of multiple sclerosis.

33. The method according to claim 25, wherein said assessing comprises
determining the behavior or fate of the human glial cells using a metric selected from the group selected from the group consisting of morphology, immunophenotype, transcriptionally-regulated reporters, gene expression profiles, mitotic rate, mitotic fraction, metabolic rate, mitochondrial function, oxidative state, telomerase activity, myelin structure or relative volume (G-ratio), apoptotic index, or net cell survival.

34. The method according to claim 33, wherein said assessing examines morphology as reflected in cell size, fiber outgrowth, length, complexity, or anchorage.

35. The method according to claim 33, wherein said assessing examines immunophenotype using immunocytochemistry, immunoblotting, flow cytometry, or fluorescence-activated cell sorting.

36. The method according to claim 33, wherein said assessing examines transcriptionally-regulated reporters using promoter/enhancer-driven reporters in enzymatic or fluorescent form.

37. The method according to claim 33, wherein said assessing examines gene expression profiles using microarrays, real-time PCR, or protein expression profiling.

38. A method of assessing in vivo response of human myelin to injury, stroke, inflammatory stimuli, myelinotoxic agents, or therapeutic agents, said method comprising:
providing a non-human mammal either with at least 30% of its glial cells in its corpus callosum being human glial cells or with at least 5% of its glial cells its brain and brain stem white matter being human glial cells;
subjecting the non-human mammal to injury, stroke, inflammatory stimuli, myelinotoxic agents, or therapeutic agents; and
assessing, as a result of said subjecting, the in vivo human myelin response to the injury, stroke, inflammatory stimuli, myelinotoxic agents, or therapeutic agents.

39. The method according to claim 38, wherein the mammal is an animal model for traumatic or ischemic injury, whereby the in vivo human myelin response to traumatic or ischemic injury is assessed.

40. The method according to claim 38, wherein the mammal is an animal model for stroke, whereby the in vivo human myelin response to stroke is assessed.

41. The method according to claim 38, wherein the mammal is an animal model for inflammatory stimuli, whereby the in vivo human glial cell response to inflammatory stimuli is assessed.

42. The method according to claim 41, wherein said inflammatory stimuli is selected from the group consisting of multiple sclerosis, transverse myelitis, and experimental allergic encephalomyelitis.

43. The method according to claim 38, wherein the non-human mammal is subjected to a myelinotoxic agent.

44. The method according to claim 38, wherein the non-human mammal is subjected to a therapeutic agent.

45. The method according to claim 44, wherein the therapeutic agent is selected from the group consisting of an agent to perturb glial or neuronal function, an agent to perturb neural transmission, an agent for non-CNS targets, an agent for treatment of epilepsy, an agent for treatment of multiple sclerosis, and an agent to promote remyelination.

46. The method according to claim 38, wherein said assessing involves determining the behavior or fate of the human glial cells using a metric selected from the group selected from the group consisting of morphology, immunophenotype, transcriptionally-regulated reporters, gene expression profiles, mitotic rate, mitotic fraction, metabolic rate, mitochondrial function, oxidative state, telomerase activity, myelin structure or relative volume (G-ratio), apoptotic index, or net cell survival.

47. The method according to claim 46, wherein said assessing examines morphology as reflected in cell size, fiber outgrowth, length, complexity, or anchorage.

48. The method according to claim 46, wherein said assessing examines immunophenotype using immunocytochemistry, immunoblotting, flow cytometry, or fluorescence-activated cell sorting.

49. The method according to claim 46, wherein said assessing examines transcriptionally-regulated reporters using promoter/enhancer-driven reporters in enzymatic or fluorescent form.

50. The method according to claim 46, wherein said assessing examines gene expression profiles using microarrays, real-time PCR, or protein expression profiling.

* * * * *